(12) United States Patent
Hsiao et al.

(10) Patent No.: US 12,419,514 B2
(45) Date of Patent: Sep. 23, 2025

(54) EYE MOVEMENT ANALYSIS WITH CO-CLUSTERING OF HIDDEN MARKOV MODELS (EMHMM WITH CO-CLUSTERING) AND WITH SWITCHING HIDDEN MARKOV MODELS (EMSHMM)

(71) Applicants: VERSITECH LIMITED, Hong Kong (CN); CITY UNIVERSITY OF HONG KONG, Hong Kong (CN)

(72) Inventors: Hui Wen Hsiao, Hong Kong (CN); Antoni Bert Chan, Hong Kong (CN)

(73) Assignees: Versitech Limited, Hong Kong (CN); City University of Hong Kong, Hong Kong (CN)

( * ) Notice: Subject to any disclaimer, the term of this patent is extended or adjusted under 35 U.S.C. 154(b) by 732 days.

(21) Appl. No.: 17/755,658

(22) PCT Filed: Nov. 4, 2019

(86) PCT No.: PCT/CN2019/115288
§ 371 (c)(1),
(2) Date: May 4, 2022

(87) PCT Pub. No.: WO2021/087651
PCT Pub. Date: May 14, 2021

(65) Prior Publication Data
US 2022/0361747 A1 Nov. 17, 2022

(51) Int. Cl.
*A61B 3/113* (2006.01)
*A61B 5/16* (2006.01)

(52) U.S. Cl.
CPC .............. *A61B 3/113* (2013.01); *A61B 5/163* (2017.08)

(58) Field of Classification Search
CPC ........... A61B 3/113; A61B 5/163; G06N 7/01
(Continued)

(56) References Cited

U.S. PATENT DOCUMENTS

| 6,102,870 A | 8/2000 | Edwards |
| 2012/0059845 A1* | 3/2012 | Covell ............... H04N 21/4394 707/769 |

(Continued)

OTHER PUBLICATIONS

Yeung, P.Y., et al., "A validation study of the Hong Kong version of Montreal Cognitive Assessment (HK-MoCA) in Chinese older adults in Hong Kong," Hong Kong Med J, Dec. 2014, 20(6):504-510.
(Continued)

*Primary Examiner* — Mohammed A Hasan
(74) *Attorney, Agent, or Firm* — SALIWANCHIK, LLOYD & EISENSCHENK

(57) ABSTRACT

Provided are an Eye Movement analysis with Hidden Markov Model (EMHMM) with co-clustering, an Eye Movement analysis with Switching Hidden Markov Models (EMSHMM) to analyze eye movement data in cognitive tasks involving stimuli with different feature layouts and cognitive state changes, a switching hidden Markov model (SHMM) to capture a participant's cognitive CN state transitions during the task and an EMSHMM to assess preference decision-making tasks with two or more cognitive states. The EMSHMM provides quantitative measures of individual differences in cognitive behavior/style, making a significant impact on the use of eye tracking to study cognitive behavior across disciplines.

7 Claims, 11 Drawing Sheets

(58) Field of Classification Search
USPC .................................................... 351/209
See application file for complete search history.

(56) References Cited

U.S. PATENT DOCUMENTS

| | | | |
|---|---|---|---|
| 2012/0106793 A1 | 5/2012 | Gershenson et al. | |
| 2015/0248470 A1* | 9/2015 | Coleman ............... | G16H 10/20 707/740 |
| 2019/0156150 A1* | 5/2019 | Krishnan ............... | G06V 40/70 |
| 2019/0221191 A1* | 7/2019 | Chhipa ................ | G09G 3/002 |
| 2021/0275013 A1* | 9/2021 | Alvarez ................ | A61B 3/08 |

OTHER PUBLICATIONS

Coviello, E., et al., "Clustering Hidden Markov Models with Variational HEM," Journal of Machine Learning Research, 2014, 15:697-747.

Govaert, G., & Nadif, M. (2013). Co-clustering: models, algorithms and applications. ISTE, Wiley. ISBN 978-1-84821-473-6.

Lau, E.Y.Y., et al., "Executive function in patients with obstructive sleep apnea treated with continuous positive airway pressure," Journal of the International Neuropsychological Society, 2010, 16:1077-1088.

Chan, C.Y.H., et al., "Eye-movement patterns in face recognition are associated with cognitive decline in older adults," Psychonomic Bulletin & Review, 2018, 25:2200-2207.

Shimojo, S., et al., "Gaze bias both reflects and influences preference," Nature Neuroscience, Dec. 2003, 6 (12):1317-1322.

Chuk, T., et al., "Hidden Markov model analysis reveals the advantage of analytic eye movement patterns in face recognition across cultures," Cognition, 2017, 169:102-117.

Kanan, C., et al., "Humans have idiosyncratic and task-specific scanpaths for judging faces," Vision Research, 2015, 108:67-76.

Andrews, T.J., et al., "Idiosyncratic characteristics of saccadic eye movements when viewing different visual environments," Vision Research, 1999, 39:2947-2953.

Poynter, W., et al., "Individuals exhibit idiosyncratic eye-movement behavior profiles across tasks," Vision Research, 2013, 89:32-38.

Zhang, J., et al., "Individuals with insomnia misrecognize angry faces as fearful faces while missing the eyes: an eye-tracking study," Sleepj, 2019, 42(2):1-11.

Phillips, L.H., et al., "Mental planning and the Tower of London task," The Quarterly Journal of Experimental Psychology, Jun. 2001, pp. 1-20.

Altman, R.M., "Mixed Hidden Markov Models: An Extension of the Hidden Markov Model to the Longitudinal Data Setting," Journal of the American Statistical Association, Mar. 2007, 102(477):1-11.

MacQueen, J. (1967). Some methods for classification and analysis of multivariate observations. In Proceedings of the Fifth Berkeley Symposium on Mathematical Statistics and Probability (pp. 281-297). Berkeley, CA: University of California Press.

Castelhano, M.S., et al., "Stable Individual Differences Across Images in Human Saccadic Eye Movements," Canadian Journal of Experimental Psychology, 2008, 62(1):1-14.

Wu, D.W.-L., et al., "The influence of personality on social attention," Personality and Individual Differences, 2014, 60:25-29.

Chuk, T., et al., "Understanding eye movements in face recognition using hidden Markov models," Journal of Vision, 2014, 14(11):1-14.

Chuk, T., et al., "Mind reading: Discovering individual preferences from eye movements using switching hidden Markov models," Cognitive Science Society, 2016, pp. 182-187.

Chuk, T., et al., "Is having similar eye movement patterns during face learning and recognition beneficial for recognition performance? Evidence from hidden Markov modeling," Vision Research, 2017, 141:204-216.

International Search Report dated Jul. 28, 2020, in International Application No. PCT/CN2019/115288.

\* cited by examiner

Group 1: Explorative

Group 2: Focused

FIGURES 4b1 – 4b4
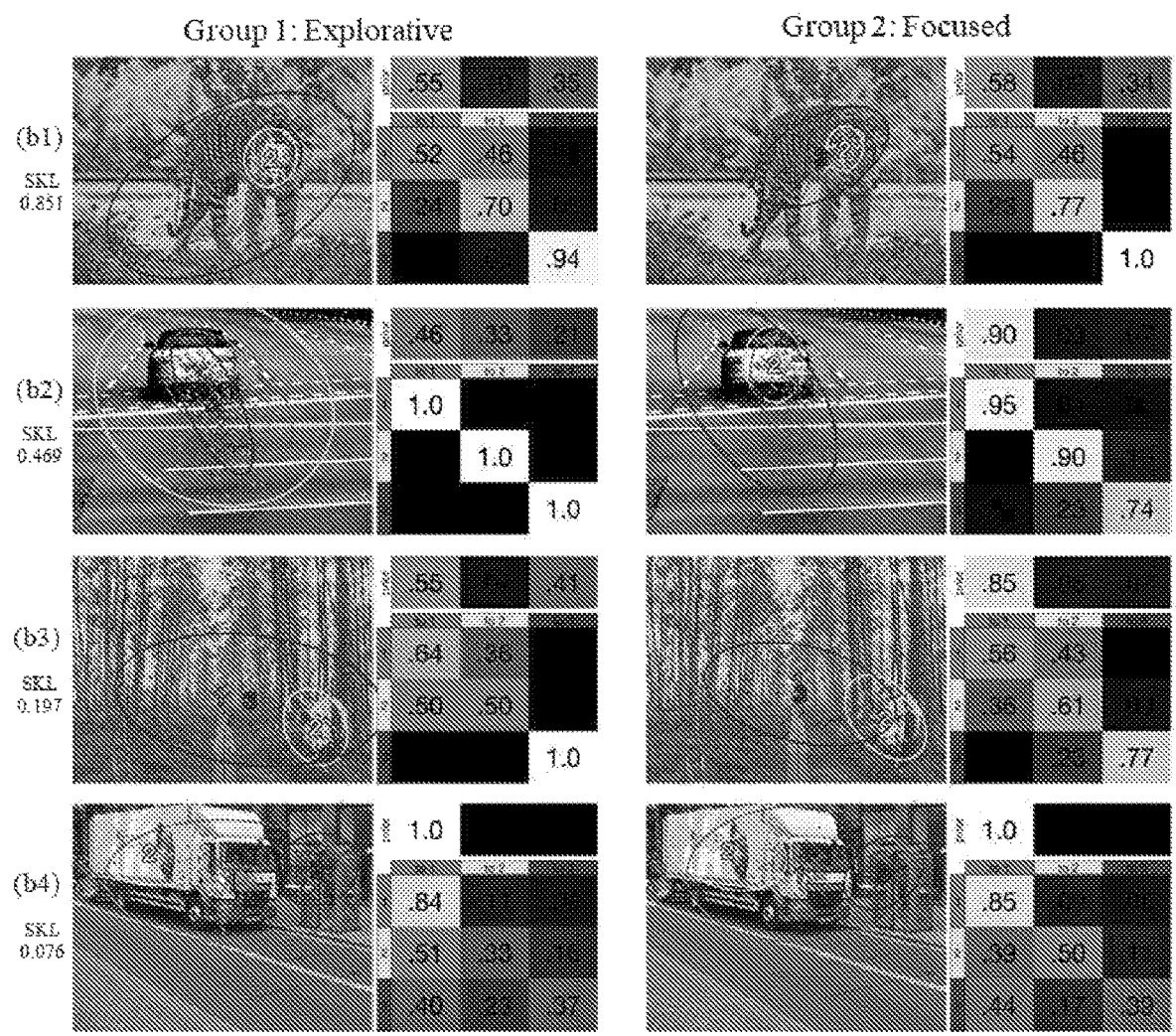

Difference

EYE MOVEMENT ANALYSIS WITH CO-CLUSTERING OF HIDDEN MARKOV MODELS (EMHMM WITH CO-CLUSTERING) AND WITH SWITCHING HIDDEN MARKOV MODELS (EMSHMM)

CROSS-REFERENCE TO RELATED APPLICATIONS

This application is the U.S. national stage application of International Patent Application No. PCT/CN2019/115288, filed Nov. 4, 2019, the disclosure of which is incorporated herein by reference in its entirety.

BACKGROUND OF THE INVENTION

Recent research has shown that people have idiosyncratic eye movement patterns in visual tasks that are consistent across different stimuli and tasks (e.g., Andrews & Coppola, 1999; Castelhano & Henderson, 2008; Poynter, Barber, Inman, & Wiggins, 2013; Kanan, Bseiso, Ray, Hsiao, & Cottrell, 2015). These idiosyncratic eye movement patterns may reflect individual differences in cognitive style or abilities. For example, it was found that participants who demonstrated higher levels of curiosity made significantly more fixations in a scene viewing task than those who demonstrated lower levels of curiosity. It was further found that when viewing human faces, those who scored higher on extraversion and agreeableness personality traits looked at the eyes significantly more often than those who scored lower (Wu et al., 2014).

In recent years, there have been attempts of using machine-learning methods to infer characteristics of the observer from eye movement data (e.g., Kanan et al., 2015). These studies typically use classifiers to discover eye movement features important for distinguishing two or more observers, and do not tell us about overall eye movement patterns associated with a particular observer. To better understand the association between eye movement patterns in visual tasks and individual differences in cognitive style or abilities, the inventors have recently developed a state-of-the-art eye movement data analysis method, Eye Movement analysis with Hidden Markov Model (EMHMM), which takes individual differences in temporal and spatial dimensions of eye movements into account (Chuk, Chan, Hsiao, 2014. EMHMM Matlab toolbox is available at http://visal.cs.cityu.edu.hk/research/emhmm/).

The EMHMM method is based on the assumption that during a visual task, the currently fixated region of interest (ROI) depends on the previously fixated ROI. Thus, eye movements in a visual task may be considered a Markovian stochastic process, which can be better understood using a hidden Markov model (HMM), a type of time-series statistical model in machine learning. More specifically, in this method, HMMs were used to directly model eye movement data, and hidden states of the HMIs corresponded to ROIs of eye movements. The transition probabilities between hidden states (ROIs) represented the temporal pattern of eye movements between ROIs. To account for individual differences, one HMM was used to model one person's eye movement pattern in a visual task in terms of both person-specific ROIs and transitions among the ROIs. An individual's HMM was estimated from the individual's eye movement data using a variational Bayesian approach that can automatically determine the optimal number of ROIs. In addition, individual HMIs could be clustered according to their similarities (Coviello, Chan, & Lanckriet, 2014) to reveal common patterns. Differences among models could be quantitatively assessed using likelihood measures, that is, by calculating the log-likelihood of data from one model being generated by another model.

Thus, the EMHMM method was particularly suitable for examining individual differences in eye movement patterns and their associations with other cognitive measures. Also, since HMM is a probabilistic time-series model, it worked well with a limited amount of data (e.g., 20 trials), which is in contrast to deep learning methods that require large amounts of data to train effectively. Thus, the EMHMM approach was especially suitable for psychological research where data availability is limited or data collection is time consuming.

The EMHMM method was successfully applied to face recognition research and discovered novel findings thus far not revealed by other methods. For example, two common eye movement patterns for face recognition were discovered: a "holistic" pattern in which participants mainly looked at the center of a face, and an "analytic" pattern that involved more frequent eye movements between the two eyes and the face center (see, e.g., FIG. 1a). Interestingly, analytic patterns were associated with better recognition performance, and this effect was consistently observed across different culture and age groups (e.g., Chuk, Chan, & Hsiao, 2017; Chuk, Crookes, Hayward, Chan, & Hsiao, 2017; Chan, Chan, Lee, & Hsiao, 2018). In addition, significantly more participants (75%) used same eye movement patterns when viewing own- and other-race faces than different patterns (Chuk, Crookes, et al., 2017). In contrast, only around 60% of participants used the same eye movement patterns between face learning and recognition, and their recognition performance did not differ significantly from those using different patterns. This is in contrast to the scan path theory, which posits that eye movements during learning have to be recapitulated during recognition for the recognition to be successful (Chuk et al., 2017).

It was further found that older adults adopted holistic patterns whereas young adults adopted analytic patterns (see, e.g., FIG. 1b). This difference was not readily observable from group eye fixation heat maps, demonstrating the power of the EMHMM method (FIG. 1c; Chan et al., 2018). Among older adults, holistic patterns were associated with lower cognitive status as assessed using Montreal Cognitive Assessment (HK-MoCA; Yeung, Wong, Chan, Leung, & Yung, 2014); particularly in executive function and visual attention abilities (as assessed by Tower of London (TOL) and Trail Making Tests). Interestingly, this association was replicated when models of the discovered common patterns were used to assess new participants' eye movement patterns when viewing new face images, suggesting the possibility of developing representative models from the population for cognitive impairment screening purposes.

Previous eye movement data analysis methods, including the use of predefined regions of interest (ROIs) or fixation heat map, did not take temporal information of eye movements into account and the use of predefined ROIs might have involved experimenter biases. Further, in these methods the analysis was typically performed on averaged or group data, and thus did not reflect individual differences in eye movement pattern. In addition, there was no quantitative measure of eye movement pattern similarity that took both spatial (eye fixation location) and temporal information (sequence of fixations) into account.

Also, the previous EMHMM method was limited to visual tasks where stimuli have the same feature layout (such as face recognition) and did not involve cognitive state changes. Therefore, novel methods are needed for quantitative measurements of eye movement patters that take spatial and temporal information into account and allow a more comprehensive prediction of human behavior based on eye movement patterns.

BRIEF SUMMARY OF THE INVENTION

Provided are methods and systems for the analysis and modeling of cognitive tasks involving cognitive state changes to predict subject behavior and/or cognitive processes. Specifically, provided is an Eye Movement analysis with Hidden Markov Model (EMHMM) with co-clustering and an Eye Movement analysis with Switching Hidden Markov Model (EMSHMM). The models of the invention measure differences in eye movement patterns by summarizing individuals' eye movements using hidden Markov models, allow discovery of common eye movement patterns, and provide quantitative measures of eye movement pattern similarities that take both temporal and spatial information of eye movements into account. Advantageously, the EMSHMM of the instant invention allows data analysis and modeling for cognitive tasks involving cognitive state changes and provides better predictions and analysis of subject behavior and cognitive processes. Furthermore, the EMHMM with co-clustering allows data analysis in tasks and cognitive behaviors that involve stimuli with different layouts, including, but not limited to, website viewing, information system usage, and visual search.

BRIEF DESCRIPTION OF THE DRAWINGS

FIG. 1A shows a holistic eye movement pattern on the left and an analytical eye movement pattern on the right. FIG. 1B shows a correlation of holistic and analytic eye movements with age. FIG. 1C shows the fixation heat maps of old participants on the left and of young participants on the right.

FIGS. 4A-C show examples of eye movement strategies. FIG. 4A shows example stimuli. FIG. 4B shows eye movement strategies for the 2 groups on the stimuli where the 2 groups use strategies that have a larger difference on the first 2 images and use strategies with a smaller difference on the last 2 images as measured by symmetric KL divergence (SKL). FIG. 4C shows heat map plots of eye fixations on the first image for the 2 groups and the difference regions in orange for Group 1 and blue for Group 2.

FIG. 5A shows the correlation between EF scale and average number of fixations. FIG. 5B shows the correlation between EF scale and average saccade length. FIG. 5C shows the correlation between EF scale and preference rating. FIG. 5D shows the correlation between EF scale and scene recognition performance in d'. FIG. 5E shows the correlation between EF scale and Flanker Congruent Acc. FIG. 5F shows the correlation between EF scale and TOL planning time before execution.

FIG. 8A shows the average probability of the two groups being in the preference-biased period throughout a trial. FIG. 8B shows the probability distribution of the number of fixations in the exploration period (top) and the number of fixations in the preference-biased period (bottom).

FIG. 9A shows the average inference accuracies using partial fixations in a trial, selected as a percentage of each trial's duration from the beginning. FIG. 9B shows the average inference accuracies of the two participant groups using different window lengths starting from the beginning of the trial.

FIG. 10A shows the average inference accuracies of two groups of participants using fixations in the last 2 seconds before the participants' response. FIG. 10B shows the relationship between participants' eye movement patterns (measured in AB scale) and the corresponding inference accuracy.

DETAILED DISCLOSURE OF THE INVENTION

Figures 1A, 1B, 1C:
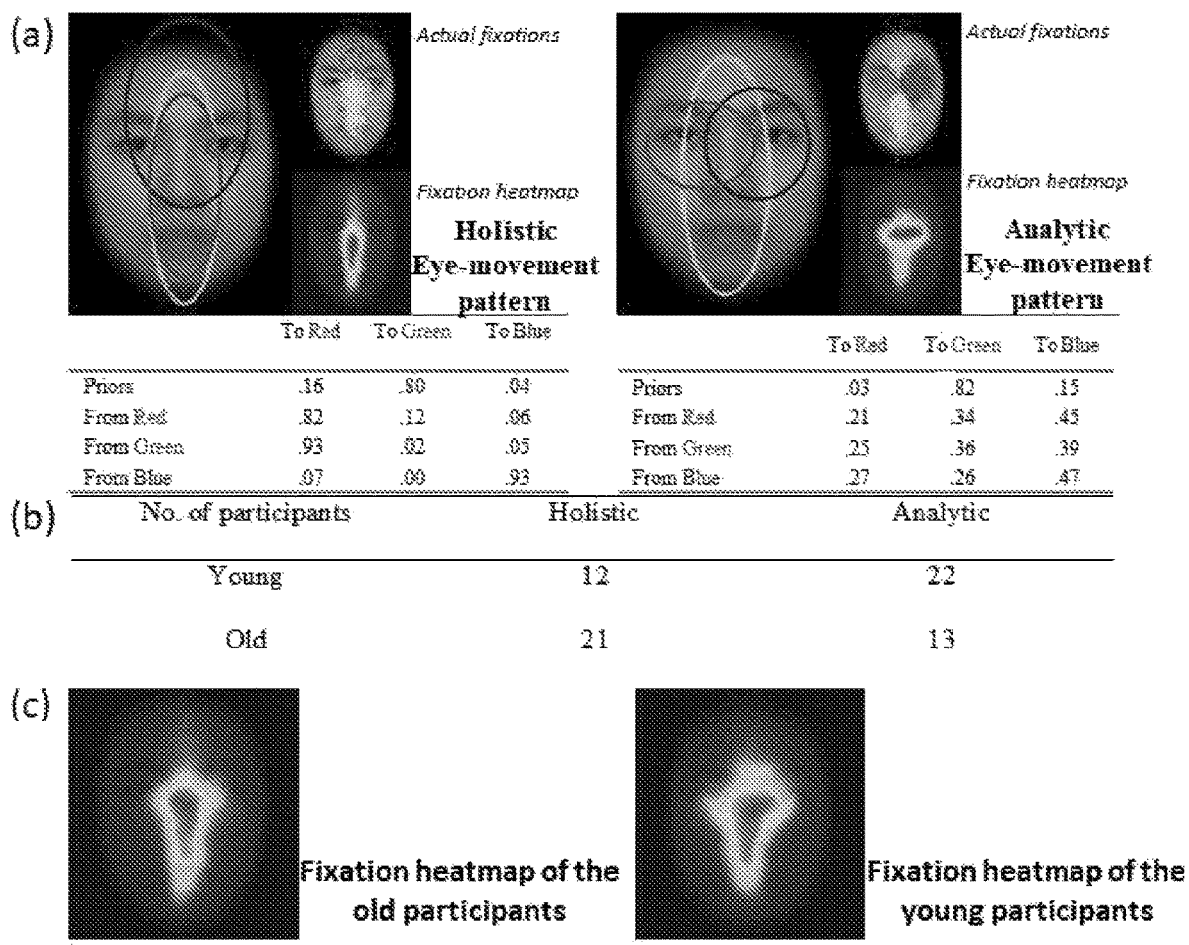
FIGS. 1A-C show the detection of two common eye movement patterns for face recognition.

Provided are methods and systems for the analysis and modeling of cognitive tasks involving cognitive state changes to predict subject behavior and/or cognitive processes.

In some embodiments, an Eye Movement analysis with Hidden Markov Model (EMHMM) with co-clustering is provided where EMHMM is combined with the data mining technique co-clustering to detect participant groups with consistent eye movement patterns across stimuli for tasks involving stimuli with different feature layouts. In specific embodiments, this model is applied to scene perception.

In some embodiments, an Eye Movement analysis with Switching Hidden Markov Model (EMSHMM) is provided to detect participant groups with consistent eye movement patters with cognitive state changes. The EMSHMM of the instant invention is particularly useful for tasks involving decision making where participants need to explore different options and decide which option they prefer; a process that involves at least two cognitive states: exploration and decision making.

Also provided are methods for determining a subject's perception style and cognitive abilities.

The EMHMM method of the invention takes individual differences in temporal and spatial dimensions of eye movements into account and uses HMMs to model eye movement data, where the hidden states of the model directly correspond to regions of interest (ROIs) of eye movements.

In some embodiments, the instant methods summarize each person's eye movement patters using an HMM in terms of both person-specific ROIs and transitions among the ROIs and clusters the individual HMIs according to their similarities. Differences among models are quantitatively assessed using likelihood measures, which reflect similarities among individual patterns.

In some embodiments, the EMHMM of the instant invention is applied to face recognition to assess cognitive status in executive and visual attention functioning and is used to assess cognitive decline or deficits. For example, using the EMHMM method of the instant invention, a perception style can be assigned to an individual based on the eye movements of the individual measured and evaluated using the EMHMM of the invention. Specific eye movement patterns measured with the EMHMM of the invention are associated with an analytic style of perception while other eye movement patterns are associated with a holistic style of perception. Furthermore, an analytic perception style is associated with improved recognition performance while a holistic perception style is associated with a cognitive decline in executive function and visual attention. Therefore, the methods of the instant invention can be used to detect cognitive performance or the decline thereof in an individual based on the individual's eye movement patterns. Importantly, the methods of the invention allow such cognitive performance assessment without the need for determining additional physiological parameters. Therefore, the methods of the invention are suitable for applications where detection of eye movement is the only data available such as in driver assessment and/or eye movement assessment via any computer or electronic device screen.

In some embodiments, the EMHMM with co-clustering of the instant invention is used to assess individuals that share similar eye movement patterns across stimuli. For example, the EMHMM with co-clustering method of the instant invention comprises the generation of individual HMMs including personalized ROIs and transition probabilities between ROIs; the determination of common patterns through clustering; the quantification of similarities between patterns using data log-likelihoods; and the use of the similarity measures to examine the relationship between eye movement patterns and cognitive measures.

In some embodiments, the EMHMM with co-clustering methods of the invention assesses individuals' eye movement patterns across stimuli during scene perception and defines an association of the eye movement patterns with foreground object recognition performance and cognitive abilities. In the EMHMM with co-clustering method of the invention the co-clustering formulation ensures that the participant groups are consistent across all stimuli and the quantitative assessment using log-likelihood measures enables the determination of the relationships of eye movement patterns with a variety of cognitive measures. Using the methods of the instant invention, types of scene images that induce larger individual differences in eye movement patterns can be determined and object recognition performance and cognitive abilities of individuals be measured based on eye movement patterns during scene viewing.

In some embodiments, EMHMMs of the instant invention use HMMs to model eye movements, where the hidden states of the HMMs are directly associated with regions of interest (ROIs) of eye movements and the temporal dynamics of eye movements are determined in terms of ROIs and transitions among ROIs.

In some embodiments, individual HMMs are clustered to detect representative strategies among subjects and co-clustering is used to cluster subjects into groups according to whether they use similar eye movement strategies across stimuli. Differences between group strategies are subsequently quantified using symmetric KL (SKL) divergence between the group HMMs. Correlations between eye movement patterns and recognition performance and/or cognitive abilities are determined by quantifying the similarities of a subject's pattern to the group strategies using a cluster score where log-likelihoods of a subject's data under the different group strategies are employed. For example, individuals' eye gazes across images are clustered into two groups using the data mining technique co-clustering resulting in two group HMMs for each image. Histograms of SKL divergence between the two general pattern groups are generated, where SKL quantifies the difference between the two group patterns for each stimulus. Preferentially, images that induce larger differences between individuals are used because larger individual differences are more likely to provide adequate variance among individuals for identifying atypical patterns.

In preferred embodiments, cognitive ability tests are used together with eye movement pattern detection. For example, a Tower of London (TOL) test is used to test for measuring executive function, a Flanker Task test is used for measuring visual attention, and a Verbal & Visuospatial Two-Back Task test is used for measuring working memory. Using these methods of the invention it has been determined that eye movement pattern in scene perception are particularly suited to measure visual attention and executive function. Therefore, in preferred embodiments, the EMHMM with co-clustering method of the invention is used to measure visual attention and executive function in individuals, where a focused eye movement pattern indicates superior visual attention and executive function compared to an explorative eye movement pattern. In further preferred embodiments, the EMHMM with co-clustering method of the invention is used to measure object recognition performance, where an explorative eye movement patterns indicates superior object recognition performance compared to a focused eye movements pattern.

In some embodiments, hierarchical HMMs are provided with at least two layers: a high-level HMM that acts like a switch that captures the transitions between cognitive states and several low-level HMMs that are used to learn the eye movement pattern of a cognitive state.

Advantageously, the models of the invention measure differences in eye movement patterns by summarizing individuals' eye movements using hidden Markov models, allow discovery of common eye movement patterns, and provide quantitative measures of eye movement pattern similarities that take both temporal and spatial information of eye movements into account. For example, the EMSHMM of the instant invention allows data analysis and modeling for cognitive tasks involving cognitive state changes and provides better predictions and analysis of subject behavior and cognitive processes. Furthermore, the methods of the invention allow data analysis in tasks and cognitive behaviors that involve stimuli with different layouts, including, but not limited to, website viewing, information system usage, visual search, driving, and other complex tasks.

In specific embodiments of the invention, the data may be received from any type of eye tracking mechanism, whether optical, electrical, magnetic, or otherwise that calculate the eye gaze position of a human eye. In preferred embodiments, the eye movements are recorded using an Eyelink 1000 eye tracker, but any eye tracking mechanism may be used in performing the instant invention without deviating from the spirit or scope of the invention. In preferred embodiments, eye tracking patterns are collected using video camera images.

In some embodiments, the data received from the eye tracking mechanisms are used in a Hidden Markov model. A Hidden Markov model is a statistical model used primarily to recover a data sequence that is not immediately observable. The model derives probability values for the unobservable data sequence by interpreting other data that depend on that sequence and are immediately observable.

In some embodiments, the Hidden Markov model of the instant invention represents the visible output, e.g., the raw data received from the eye-tracking mechanism as a randomized function of the invisible internal state, e.g., the cognitive state of a subject.

The Hidden Markov model can be used to model visual attention or eye movement changes corresponding to transitions in cognitive states during a complicated cognitive task.

In specific embodiments of the instant invention, HMMs are used directly to model eye movements, and hidden states of the HMMs are directly associated with ROIs of eye movements. This allows the determination of temporal dynamics of eye movements in terms of ROIs and transitions among ROIs specific to an individual.

Advantageously, the novel methods of the instant invention detect multiple cognitive states that occur during a task and the eye movement pattern associated with each cognitive state; thus allowing a better understanding of individual differences in eye movement patterns in real-life complicated cognitive tasks and predicting cognitive states from eye movement patterns.

In some embodiments, the instant invention provides switching HMIs (SHMMs) that are hierarchical HMMs with two layers containing a high-level HMM and several low-level HMIs. Each low-level HMM can be used to learn the eye movement pattern of a cognitive state. The high-level HMM acts like a 'switch' that captures the transitions between cognitive states. It does so by learning the transitions between the low-level HMMs.

The SHMMs of the instant invention are used to model transitions between cognitive states and their associated eye movement patterns in a cognitive task.

In some embodiments, the high-level states represent the cognitive states, whereas the low-level states correspond to ROIs over the stimuli.

In some embodiments, eye movements are modeled in a preference decision making task using face preference decision making in which participants are presented with two face images in each trial and asked to judge which face they like more. According to embodiments of the invention, at least two different eye movement patterns are observed one involving no fixation preference over either stimulus, which is related to exploration and information sampling, whereas the other involving a higher percentage of fixations over the to-be-chosen stimulus, which both reflects and shapes a participant's preferences.

In specific embodiments, SHMM is used to capture the dynamics in cognitive state and eye movement pattern. In some embodiments, one SHMM per individual is trained to summarize an individual's eye movement behavior during a task. In some embodiments, two or more SHMMs are trained using data from two different participant selections.

In preferred embodiments, individual SHMMs according to their similarities are clustered to discover common eye movement patterns in a task. Different eye movement patterns are associated with different decision-making behavior and can be detected and measured with the methods and systems of the instant invention. Thus, the methods of the instant invention can be used to infer, e.g., a decision making behavior from eye movement patterns.

In some embodiments, the EMHMM with co-clustering is used to discover common patterns in participant groups and analyze tasks or cognitive behavior involving stimuli with different layouts, including, but not limited to, website viewing, information system usage, and visual search. Further tasks or cognitive behaviors that can be analyzed using the methods of the invention are reading, picture viewing, video viewing, scene viewing, driving, navigation, and others.

Advantageously, the methods of the instant invention enable the assessment of more than one cognitive state in complex tasks and allow the identification of said cognitive states based on the measured eye movement patterns.

In preferred embodiments, specific eye movement patterns of a specific cognitive state are used to identify in a subject a certain cognitive state.

In further embodiments, systems are provided to perform the methods of the instant invention. In some embodiments, the systems comprise a camera and a processor configured to detect an eye position within a facial image captured by the camera. In some embodiments, the processor is further configured to perform the steps and/or algorithms of the instant invention. In preferred embodiments, the processor is configured to read and process data from the camera according to a Matlab toolbox to analyze HMIs, EMHMMs, and EMSHMMs.

In some embodiments, an electronic device is provided that comprises a camera and a processor configured to detect a center position of an eye within a facial image captured via the camera in response to detecting an eye within the facial image; determine an eye gaze position based on the center position and a pupil position; analyse the eye gaze position in consecutively captured facial images; and measure an eye movement patterns based on the eye gaze positions of the consecutively captured facial images.

In specific embodiments, the processor is further configured to generate an exploration transition matrix and Gaussian emission for each subject. In some embodiments, the processor is further configured to cluster or summarize HMMs into single groups using a Variational Hierarchical Expectation Maximization algorithm, wherein the HMMs are clustered according to their probability distributions. In other embodiment the processor is further configured to assimilate external user-entered data to associate certain eye movement patterns with certain external task criteria or cognitive state criteria.

In further embodiments, the processor is configured to determine the number of fixations of eye movements. Advantageously, from the eye movement pattern and fixation probability distributions, the systems of the instant invention can calculate a probability of an individual being in a certain cognitive state.

In some specific embodiments, the system of the invention can be used to infer an individual's preference for a certain choice based on the eye movement patterns.

In some embodiments, the system of the invention can be used to determine an individual's cognitive style based on the eye movement patterns of the individual. In specific embodiments, the processor of the system is configured to calculate a log likelihood of a eye movement pattern and assign a certain cognitive style to the measured eye movement pattern if it matches the eye movement pattern of a representative group of individuals having said cognitive style.

Further provided are methods for inferring an individual's preference choice using eye movement patterns. In specific embodiments, the individual's preference choice is inferred from the individual's eye movement fixations measured in different time intervals from the beginning of a trial to the making of a preference choice at the end of the trial. In specific embodiments, the individual's preference choice is inferred from the individual's eye movement fixations measured during the last 25% of the time interval from the beginning of a trial. In preferred embodiments, the individual's preference choice is inferred from the individual's eye movement fixations measured during the last 15% of the time interval from the beginning of a trial. In more preferred embodiments, the individual's preference choice is inferred from the individual's eye movement fixations measured in the last 10% of the time interval from the beginning of a trial. In most preferred embodiments, the individual's preference choice is inferred from the individual's eye movement fixations measured in the last 5% of the time interval from the beginning of a trial.

Further provided are methods for inferring an individual's preference choice using eye movement patterns measured at different time intervals before a choice response. In specific embodiments, the individual's preference choice is inferred from the individual's eye movement fixations measured in the last 10 seconds before the choice response. In preferred embodiments, the individual's preference choice is inferred from the individual's eye movement fixations measured in the last 8 seconds before the choice response. In other preferred embodiments, the individual's preference choice is inferred from the individual's eye movement fixations measured in the last 6 seconds before the choice response. In more preferred embodiments, the individual's preference choice is inferred from the individual's eye movement fixations measured in the last 4 seconds before the choice response. In most preferred embodiments, the individual's preference choice is inferred from the individual's eye movement fixations measured in the last 2 seconds before the choice response.

Advantageously, the instant methods enable the measurement of individual differences in eye movement patterns and cognitive styles during complex cognitive tasks. Furthermore, the instant methods allow the measurement of an individual's preferences significantly earlier than previously used methods. Specifically, the instant methods enable a measurement of an individual's choice preference with only the first 75% of fixations that precede the choice.

Advantageously, the accuracy in inferring an individual's preference choices using the methods of the instant invention, particularly using EMSHMM, is significantly higher than that using, e.g., EMHMM.

Furthermore, the EMHMM with co-clustering of the invention can be used to infer an individual's cognitive style and/or cognitive abilities.

Importantly, the methods of the instant invention enable inferring an individual's preference choice and cognitive style/abilities from eye gaze information alone using EMSHMM and/or EMHMM with co-clustering without the need for further additional physiological information, making the instant methods and systems especially suited for applications where eye movement measurements are the only data obtained from an individual to determine the individual's cognitive style, inferring an individual's preference choice and/or measuring an individual's cognitive abilities.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods

Example 1—Use of Eye Movement Analysis with Hidden Markov Models (EMHMM) in Face Recognition Using the EMHMM approach, the inventors previously detected holistic and analytic eye movement patterns in face recognition through clustering of eye movement patterns in 34 young and 34 older adults (Chan, Chan, Lee, and Hsiao (2018)). In the representative models, ellipses show ROIs corresponding to 2-D Gaussian emissions (FIG. 1A). Prior values show the probabilities that a trial starts from the ellipse/ROI. Transition probabilities show the probabilities of observing a particular transition to the next ROI from the current ROI. The small images on the right show the assignment of actual fixations to the ROIs and the corresponding fixation heatmaps. Note that the clustering algorithm (Coviello, Chan, & Lanckriet, 2014) summarizes individual models in a cluster into a representative HMM using a pre-specified number of ROIs, which may result in overlapping ROIs. Here the number of ROIs in the representative models was set to 3, the median number of ROIs in the individual models. FIG. 1B shows the frequency of young and older adults adopting holistic and analytic patterns: significantly more older adults adopted holistic patterns and more young adults adopted analytic patterns. FIG. 1C shows group fixation heat maps of older and young adults.

Example 2—Use of EMHMM with Different Stimuli

Because the EMHMM method providing quantitative measures of individual differences in eye movement pattern is limited to tasks where stimuli have the same feature layout (e.g., faces), a novel method was developed that combines EMHMM with the data mining technique co-clustering to detect participant groups with consistent eye movement patterns across stimuli for tasks involving stimuli with different feature layouts. This novel method was applied to scene perception. Using the novel EMHMM with co-clustering method of the invention, explorative (switching between foreground and background information) and focused (mainly on foreground) eye movement strategies were detected. Explorative patterns were associated with better foreground object recognition performance whereas those with focused patterns had better feature integration in the flanker task and more efficient planning in the Tower of London (TOL) task. Advantageously, these novel methods can be used to employ eye tracking as a window into individual differences in cognitive abilities and for screening of cognitive deficits.

Scene perception involves complex and dynamic perceptual and cognitive processes that can be influenced by both observers' goals and diverse scene properties at multiple levels. Eye movements during scene perception reflect the complexity of cognitive processes involved, and thus can potentially provide rich information about individual differences in perception styles and cognitive abilities. For example, it was observed that Westerners made more eye fixations on foreground objects whereas Asians looked at the backgrounds more often, and this difference was reflected in their foreground object recognition performance. This phenomenon has been linked to cultural differences in perception styles: Westerners are more likely to attribute the cause of an event to isolated objects (analytic style), whereas Asians are more likely to attribute the cause of an event to the context of the event (holistic style). However, these effects have not been found consistently and some studies found no difference between American and Chinese participants either in foreground object recognition performance or in number of fixations and durations to the foreground and background. Thus, it remains unclear whether eye movement patterns consistently reflect cultural differences in perception styles and individual differences in cognitive abilities.

Previous studies have attempted to use machine-learning methods to infer characteristics of the observer from eye movement data. These studies typically used classifiers to discover eye movement features important for distinguishing two or more observers. However, the classifiers only look for features important for separating the observers, and do not provide any information about eye movement patterns associated with a particular observer. The EMHMM approach, where HMM is a type of time-series statistical model, has been developed by the inventors. This approach takes individual differences in temporal and spatial dimensions of eye movements into account. EMHMM assumes that during a visual task, the currently fixated region of interest (ROI) depends on the previously fixated ROI. Thus, eye movements may be considered a Markov stochastic process, which can be better understood using HMMs. Other studies have used HMMs/probabilistic models for modeling eye movement/visual attention and cognitive behavior, where hidden states of the models represented cognitive states. In contrast, EMHMM of the instant invention directly uses HMMs to model eye movement data, and hidden states of the models directly correspond to ROIs of eye movements. To account for individual differences, each person's eye movement pattern is summarized using an HMM in terms of both person-specific ROIs and transitions among the ROIs, estimated from the individual's data using a variational Bayesian approach that can automatically determine the number of ROIs. Individual HMMs are clustered according to their similarities to reveal common strategies. Differences among models are quantitatively assessed using likelihood measures, which reflect similarities among individual patterns. Thus, this method is particularly suitable for examining individual differences in eye movement patterns and their associations with other cognitive measures. Furthermore, because EMHMM is a Bayesian probabilistic model it works well with limited amounts of data; in contrast to deep learning methods that require large amounts of data to train effectively. The EMHMM of the instant invention has been applied to face recognition research, discovering novel findings thus far not revealed by existing methods. For example, two common eye movement strategies were identified: analytic (more eyes-focused) and holistic nose-focused (FIG. 1A). Asians and Caucasians did not differ significantly in the frequency of adopting the two strategies, suggesting little modulation from culture (Chuk et al., 2017). Analytic patterns were associated with better recognition performance, suggesting that retrieval of diagnostic information (i.e., the eyes) is a better predictor for performance (Chuk, Chan, & Hsiao, 2017). In contrast, older adults adopted holistic patterns compared to young adults, and their holistic patterns were associated with lower cognitive status particularly in executive and visual attention functioning: the more holistic (nose-focused) the pattern, the lower the cognitive status (Chan, Chan, Lee, Hsiao, 2018). This correlation was replicated with new participants viewing new face images using the group HMMs discovered from the old participants, suggesting the possibility of developing representative HMMs from the population for cognitive screening purposes. Similarly, insomniacs' impaired ability for facial expression judgments was associated with usage of a less eye-focused pattern, suggesting that impaired visual attention control may account for compromised emotional face perception in insomniacs (Zhang et al., 2019). Together these results suggest the possibility of using eye tracking as a screening assessment for cognitive decline or deficits.

EMHMM has been limited to tasks involving stimuli with the same feature layout so that discovered ROIs correspond to the same features across stimuli. For tasks where stimuli have different layouts, the inclusion of perceived images as features in the ROI representations has been proposed but, while this method has improved discovery of ROIs, it does not work well when features among stimuli differ significantly, such as in scene perception.

Example 3—Novel EMHMM with Co-Clustering

Figure 2:
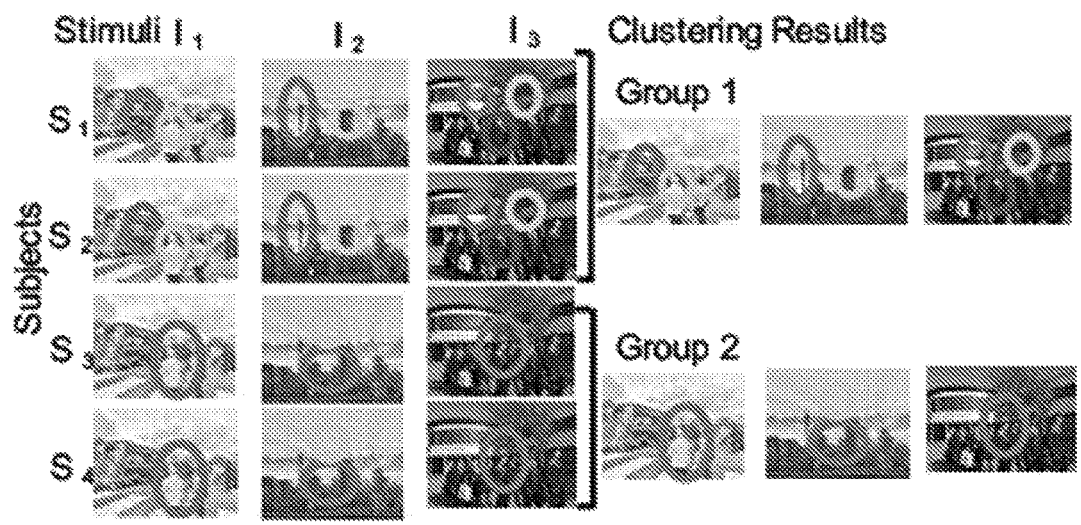
FIG. 2 shows an example of EMHMM with co-clustering of the invention. Circles indicate ROIs.

The instant invention provides a new method that models each participant's eye movements when viewing a particular stimulus with one HMM, and uses the data mining technique co-clustering (see, e.g., Govaert & Nadif, 2013) to detect subjects sharing similar eye movement patterns across stimuli. The co-clustering formulation ensures that the subject groups are consistent across all stimuli. The result is a grouping of subject and their representative HMIs for each stimulus (FIG. 2). The similarity between an individual's eye movement patterns across stimuli and the representative HMMs are quantitatively assessed using log-likelihood measures as in the existing approach. The results are used to examine the relationship between eye movement patterns and other cognitive measures. Using this method, individual differences in eye movement patterns during scene viewing were examined and it was determined (1) what types of scene images (animals in nature vs. vehicles in a city) induce larger individual differences in eye movement patterns, and (2) how eye movement patterns during scene viewing are associated with subsequent foreground object recognition performance and cognitive abilities among subjects.

In a study, 61 Asian participants (35 females) aged 18-25 (M=20.77, SD=1.70) were recruited from the University of Hong Kong. All participants had normal or corrected-to-normal vision. The materials viewed consisted of 150 scene images with animals in a natural environment and 150 scene images with vehicles in an urban environment. Images with different numbers of foreground objects, feature layouts, and locations of foreground objects were used to increase stimulus variability to provide adequate opportunities to elicit individual differences in eye movement pattern.

The scene perception task consisted of a passive viewing phase and a surprise recognition phase (following Chua et al., 2005). During the passive viewing phase, for each scene type (animals vs. vehicles), participants were presented with 60 images one at a time, each for 5 seconds, and rated from 1 to 5 how much they liked the image. During the surprise recognition phase, for each scene type, participants were presented with 60 images with old foreground objects, with half of them presented in the same old background and the other half in a new background, together with the same number of lure images with new objects in a new background. Participants were presented with the images one at a time, and they judged whether they saw the foreground object during the passive viewing phase. The image stayed on the screen until response. In both phases the animal and vehicle scene images were presented in 2 separate blocks, with the block order counterbalanced across participants. Participants' eye movements were recorded using an Eye-Link 1000 eye tracker, with a chinrest to minimize head movements. Each trial started with a fixation cross at the screen center. The experimenter initiated the image presentation when a stable fixation was observed at the fixation cross. An image was then presented at the screen center, spanning 35°×27° of visual angle at a viewing distance of 0.6 m. Before each block, a 9-point calibration procedure was performed. Re-calibration took place whenever drift correction error exceeded 1° of visual angle.

In addition, participants performed 3 cognitive tasks to examine whether their eye movement patterns were associated with cognitive abilities:

(1) Tower of London (TOL) task (see, e.g., Phillips et al., 2001) for testing executive function/planning abilities: In each trial, participants saw 3 beads randomly placed on 3 pegs as the starting position, together with the target position. They were asked to move 1 bead at a time to reach the target position as quickly as possible with the minimum number of moves and to plan the moves in mind before execution. In total there were 10 trials. The total number of extra moves, number of correct trials, total planning time before executing the first move, and total execution time for the moves were measured.

(2) Flanker task (see, e.g., Ridderinkhof, Band, & Logan, 1999) for testing selective attention: Participants judged the direction of an arrow flanked by 4 other arrows. In the congruent condition, the flanking arrows pointed at the same direction as the target arrow, whereas in the incongruent condition, the flanking arrows pointed at the opposite direction. In the neutral condition, the flankers were non-directional symbols.

(3) Verbal and visuospatial 2-back task for assessing working memory capacity (see, e.g., Lau et al., 2010): In each trial, participants judged whether the presented symbol/ symbol location was the same as the one presented 2 trials back in the verbal/visuospatial task respectively.

Participants' eye movements during the passive viewing phase were analyzed using EMHMM with co-clustering (adapted from http://viral.cs.cityu.edu.hk/research/ emhmm). Each participant's eye movements for viewing each stimulus were summarized using an HMM. Individual HMMs for viewing each stimulus were clustered to discover 2 representative strategies among the participants. Co-clustering was then used to cluster participants into 2 groups according to whether they used similar eye movement strategies across the stimuli (FIG. 2). To examine whether natural or man-made images could induce larger individual differences in eye movement pattern, the difference between group strategies for each stimulus were quantified via the symmetric KL (SKL) divergence between the two group HMMs. The SKL is given by $(KL_{12}+KL_{21})/2$, where $KL_{12}$ is the KL divergence between the Group 1 HMM and the Group 2 HMM using Group 1 data (Chuk, Chan, & Hsiao, 2014), and vice-versa for $KL_{21}$ (KL is not symmetric). SKL measures were compared for natural and man-made images and the characteristics of the images that typically led to larger SKL were determined.

It was also examined whether the 2 groups of participants differed in performance in foreground object recognition and the cognitive tasks. To examine the correlations between eye movement pattern and recognition performance/cognitive abilities, the similarity of a participant's pattern to the group strategies were examined using a cluster score, $CS=(|L_1|-|L_2|)/(|L_1|+|L_2|)$, where $L_1$ and $L_2$ are the log-likelihoods of a participant's data being generated under Group 1 and Group 2 strategy, respectively (Chan et al., 2018). Larger positive values of CS indicate higher similarity to Group 1, and smaller negative values indicate similarity to Group 2.

Figure 3:
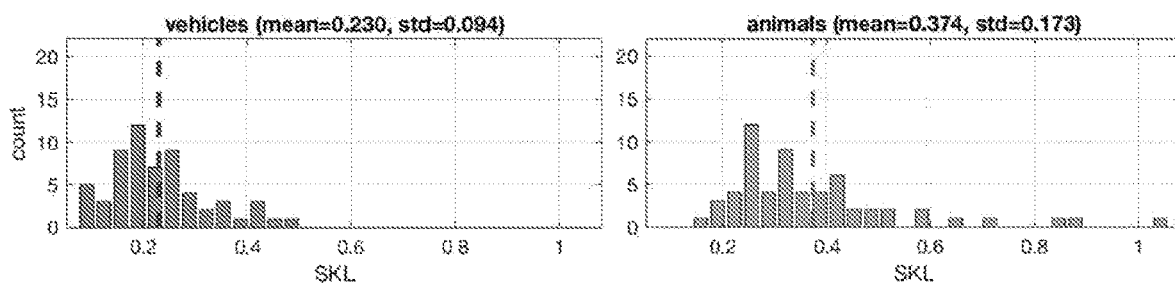
FIG. 3 shows histograms of symmetric KL (SKL) divergence between Group 1 and Group 2 strategies on vehicle or animal images.
Figure 4A:
Figure 4A:
Figure 4A:
Figure 4C:
Figures 5A, 5B, 5C, 5D, 5E, 5F:
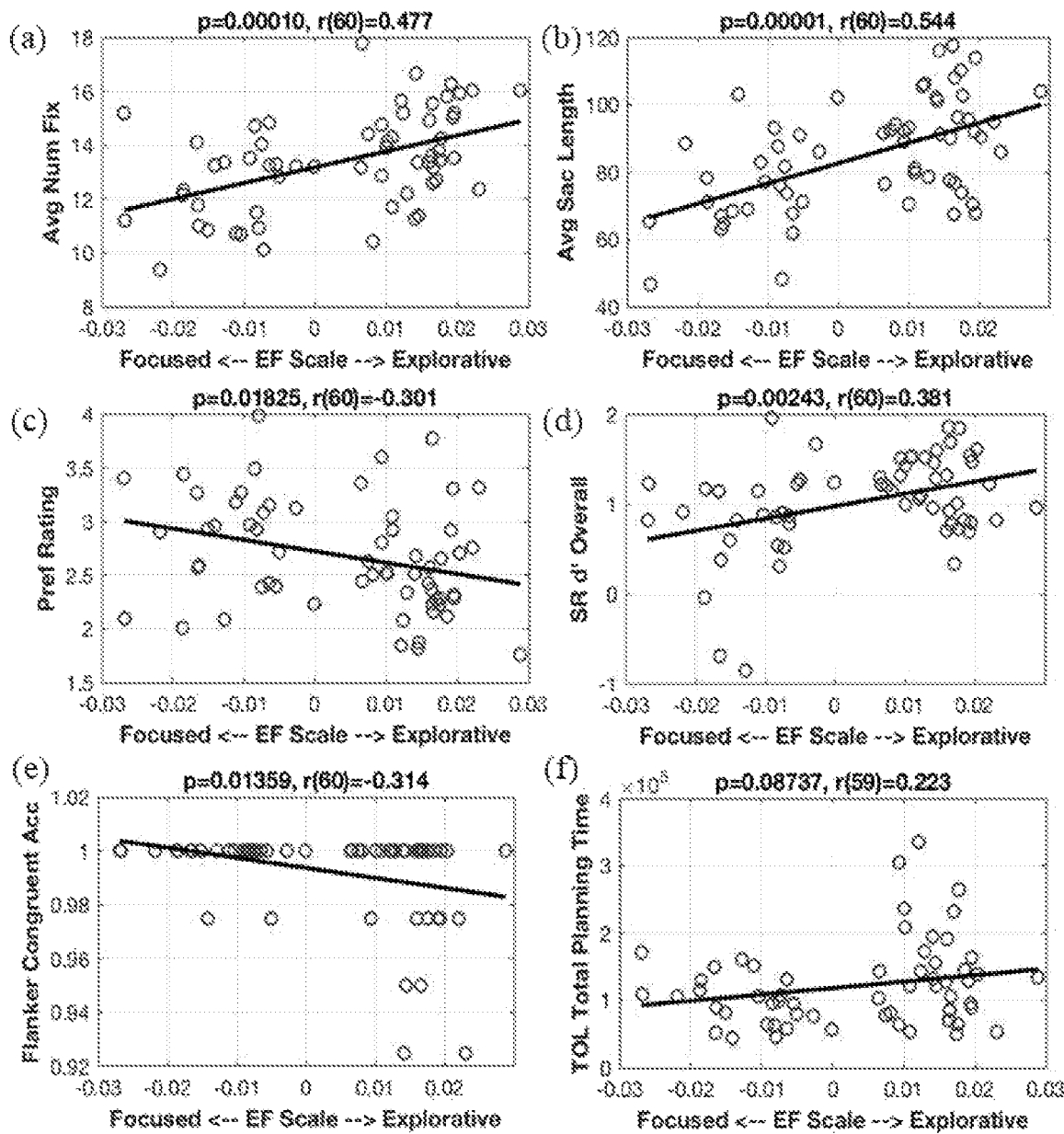
FIGS. 5A-F show correlation analyses.

Example 4—Eye Movement Strategies in Scene Perception Determined Using EMHMM with Co-Clustering The data obtained as described in Example 3 from 61 participants were clustered into 2 groups using EMHMM with co-clustering on the 120 image stimuli. Group 1 contained 37 participants and Group 2 contained 24 participants. The co-clustering model estimates 2 HMMs for each image stimulus, corresponding to the strategies of Groups 1 and 2. For each image, the difference between the strategies was measured in SKL. As shown in FIG. 3, animal images induced larger differences in eye movement strategies between the 2 groups than vehicle images, $t(118)=-5.626$; $p<0.0001$. FIG. 4A presents 4 example images and their corresponding HMMs for the 2 groups. FIGS. 4b1 and 4b2 show two examples of eye movement strategies with large SKL difference between the 2 groups. In particular, Group 2 focused more on the foreground object, while Group 1 explored the image, looking at both the foreground object and the background. In addition, while looking at an animal, Group 2 focused more on the eyes, whereas Group 1 looked at the nose (FIG. 4c). FIGS. 4b3 and 4b4 show examples where the 2 groups had similar eye movement strategies. In general, larger differences in eye movements occurred on images where the foreground object (animal or car) was salient as compared with the background, e.g., an animal among trees, or a car on a road. This indicates that animals are more salient than vehicles, and that animal images generally induce larger differences in eye movement strategies than vehicle images. In contrast, images with cluttered backgrounds and non-interesting foreground objects typically induced similar eye movement strategies. Group 1 and 2 strategies are referred to as the explorative and focused strategy, respectively, and the cluster score between the two strategies as the Explorative-Focused (EF) scale. Indeed, participants using the explorative strategy had a larger average number of fixations, $t(59)=3.793$, $p<0.001$, and longer saccade lengths, $t(59)=4.881$, $p<0.001$, than those using the focused strategy (Table 1 below), and the more similar their eye movement pattern to the explorative strategy (in EF scale), the larger the average number of fixations, $r(60)=0.477$, $p<0.001$, and saccade length, $r(60)=0.544$, $p<0.001$ (FIGS. 5a-e). As EMHMM does not use sequence length information, the difference in average number of fixations emerged naturally as the result of the clustering. These results were consistent with the interpretation that Group 1 was more explorative than Group 2.

TABLE 1

Comparison of eye movement statistics and cognitive task performance between the explorative and focused strategies (FOR: Foreground Object Recognition).

| Task Measure | Group 1 Explorative | | Group 2 Focused | | | |
|---|---|---|---|---|---|---|
| | mean | std | mean | std | p | t |
| Avg Number of Fixations | 14.06 | 1.659 | 12.43 | 1.602 | 0.000 | 3.793 |
| Avg Fixation Duration | 312.4 | 43.23 | 335.9 | 66.77 | 0.100 | −1.672 |
| Avg Saccade Length | 91.92 | 13.87 | 74.34 | 13.56 | 0.000 | 4.881 |
| Image Preference Rating | 2.545 | 0.485 | 2.890 | 0.496 | 0.009 | −2.689 |
| FOR Reaction Time (RT) | 1160 | 303.4 | 1216 | 412.4 | 0.545 | −0.609 |
| FOR d' Original Background | 1.695 | 0.556 | 1.050 | 0.922 | 0.001 | 3.410 |
| FOR d' New Background | 0.802 | 0.302 | 0.531 | 0.406 | 0.004 | 2.986 |
| FOR d' Overall | 1.203 | 0.356 | 0.766 | 0.638 | 0.001 | 3.434 |
| N-back Verbal d' | 2.867 | 0.550 | 2.640 | 0.725 | 0.169 | 1.391 |
| N-back Verbal RT | 731.8 | 169.2 | 706.2 | 127.6 | 0.529 | 0.633 |
| N-back Spatial d' | 2.244 | 0.764 | 2.201 | 0.594 | 0.819 | 0.230 |
| N-back Spatial RT | 780.2 | 220.3 | 742.9 | 146.2 | 0.468 | 0.730 |
| Flanker Incongruent Acc | 89.26 | 14.79 | 90.21 | 19.56 | 0.830 | −0.216 |
| Flanker Congruent Acc | 98.85 | 2.091 | 99.79 | 0.706 | 0.038 | −2.121 |
| Flanker Neutral Acc | 97.97 | 3.272 | 97.81 | 3.240 | 0.852 | 0.188 |
| Flanker Overall Acc | 95.36 | 5.331 | 95.4 | 6.677 | 0.710 | −0.374 |
| Flanker Incongruent RT | 414.8 | 47.03 | 415.3 | 99.80 | 0.980 | −0.025 |
| Flanker Congruent RT | 362.5 | 35.08 | 373.1 | 36.37 | 0.261 | −1.135 |
| Flanker Neutral RT | 366.0 | 37.88 | 373.6 | 36.39 | 0.440 | −0.778 |
| Flanker Overall RT | 381.1 | 38.23 | 387.4 | 48.54 | 0.579 | −0.558 |
| TOL Total # Moves | 24.97 | 17.00 | 26.29 | 18.79 | 0.779 | −0.282 |
| TOL # Correct Trials | 5.194 | 2.550 | 4.875 | 2.983 | 0.659 | 0.444 |
| TOL Total Executaion Time (s) | 177.7 | 69.23 | 181.8 | 77.44 | 0.829 | −0.216 |
| TOL Preplanning Time (s) | 137.0 | 71.33 | 99.21 | 36.27 | 0.020 | 2.395 |

Example 5—Association Between Eye Movement Pattern and Recognition Performance/Cognitive Abilities Using EMHMM with Co-Clustering Participants using the explorative strategy also had significantly lower image preference ratings, t(59)=−2.689, p=0.009; better foreground object recognition in d', t(59)=3.434, p=0.001; lower accuracy in congruent trials of the flanker task, t(59)=−2.121, p=0.038; and longer total planning time before execution in the TOL task, t(58)=2.395, p=0.02 (Table 1; one participant's TOL result was missing due to technical problem). Note that their advantage in foreground object recognition performance was significantly larger when the foreground object was presented with the original background than with a new background, F(1, 59)=9.126, p=0.004, although the advantage was significant in both cases (Table 1). Consistent with these findings, correlation analysis showed that participants' eye movement pattern similarity to the explorative strategy (EF scale) was correlated negatively with preference ratings, r(60)=0.301, p=0.018; positively with scene recognition performance in d', r(60)=0.381, p=0.002; and marginally positively correlated with TOL planning time before executing moves, r(59)=0.223, p=0.08 (FIGS. 5a-e). Taken together these findings indicate that the explorative strategy is associated with lower image preference rating, better scene recognition performance, decreased facilitation from consistent surrounding cues in the flanker task, and less efficient planning in the TOL task.

Overall, for images containing animal faces, participants adopting the focused strategy (analytic style) looked more to the eyes of the animal faces, suggesting engagement of local attention. In contrast, those adopting the explorative strategy (holistic style) looked more to the animal face center, suggesting engagement of global processing. These results are generally consistent with Caucasians' analytic style that is associated with focusing on the foreground object in scene perception and the eyes in face recognition, whereas Asian's holistic style is associated with looking more often at the background and the face center. However, using EMHMM, the inventors showed that Asians and Caucasians did not differ in the frequency of adopting the eyes-focused or nose-focused strategy, suggesting little modulation from culture on eye movement pattern when individual difference was taken into account (Chuk et al. 2017).

It was observed that participants adopting the explorative strategy had better foreground object recognition performance than those using the focused strategy, regardless of whether the foreground object appeared in a new or old background; this advantage was larger when the foreground object appeared in the old than a new background. The finding suggests that a more explorative eye movement strategy during scene perception may be beneficial for remembering the foreground object due to more retrieval cues available through exploration. Consistent with this suggestion, it has been shown that associative processing is inherent in scene perception suggesting that an explorative strategy may facilitate associative processing and consequently enhance scene memory. This finding is in contrast to the face recognition literature, where the eye-focused strategy, which is associated with engagement of local attention and the focused strategy reported here, was reported to lead to better recognition performance due to better retrieval of diagnostic features, the eyes.

In contrast, using the methods of the invention, it was shown that those adopting the focused strategy performed better in the congruent trials of the flanker task and had shorter preplanning time in the TOL task than those using the explorative strategy. The advantage observed in the congruent but not incongruent or neutral trials in the flanker task suggested that these participants might have better feature integration abilities. The shorter preplanning time in the TOL task without differences in number of moves, correct trials, or execution time suggested that they had more efficient planning abilities. Thus, because participants adopting the focused strategy preferred to look at the eyes of the animals, the focused strategy may be related to a more eyes-focused strategy in face recognition, which was associated with better face recognition performance, visual attention (the trail making task), and executive function (the TOL task; Chan et al., 2018).

Using the methods of the invention it was also observed that images with a salient foreground object relative to the background tended to induce large individual differences in eye movement patterns, and that animal images induced larger individual differences than vehicle images (FIG. 3). This phenomenon may be due to humans' category specific attention to animals that made them more salient than vehicles or other object types, providing better opportunities to induce the difference between the explorative and focused strategies. This finding has important implications for the possibility of using eye tracking to provide screen tools for cognitive disorders because images that induce larger individual differences will be more likely to provide adequate variance among individuals for identifying atypically patterns.

In conclusion, it was show that the novel EMHMM with co-clustering method of the invention can effectively summarize and quantitatively assess individual differences in eye movement strategies in tasks involving stimuli with different feature layouts, and in turn lead to new discoveries not yet found by existing methods. By applying the novel method to scene perception, the explorative and focused strategies among Asians were detected. Whereas the explorative strategy was associated with better foreground object recognition performance, the focused strategy was associated with better feature integration and planning abilities. Also, images with a salient foreground object relative to the background induced larger individual differences in eye movement patterns. These results have important clinical and educational implications for the use of eye tracking in cognitive deficit detection and cognitive performance monitoring. Advantageously, the novel EMHMM with co-clustering method of the invention can be applied to a large variety of visual tasks and be instrumental in using eye movement patterns to understand cognitive behavior.

Example 6—Eye Movement Analysis with Switching Hidden Markov Models (EMSHMM) in the Detection of Different Cognitive States Using a Face Preference Decision-Making Task In previous probabilistic approaches to model visual attention in a complicated cognitive task, the hidden states of the models represented cognitive states, thus capturing the temporal dynamics of cognitive state transitions but not the dynamics of eye movements. In order to measure multiple cognitive states that occur during a task and the eye movement patterns associated with each cognitive state an EMHMM with hierarchical HMMs is used. For example, the hierarchical HMM with two layers contains a high-level HMM and several low-level HMIs. Each low-level HMM acts like a "switch" that captures the transitions between cognitive states. It does so by learning the transitions between the low-level HMMs. This method of the instant invention is called a Switching HMM (SHMM). The SHMM of the invention is used to capture the dynamics in cognitive state and eye movement pattern following an existing EMHMM approach and training one SHMM per participant to summarize the participant's eye movement behavior during a task. The individual SHMMs are then clustered according to their similarities to detect common eye movement patterns in the task and examine the different eye movement patterns associated with different decision-making behaviors.

Applying the novel EMSHMM of the instant invention, eye movement data were collected from a face preference decision-making task and two participant groups were compared. The preference decision-making task was a two-alternative-forced-choice task, which contained two parts. In part 1, participants were presented with 120 (female and male) computer generated, bald faces. They were asked to rate, from 1 to 7, how attractive the faces were. These ratings were used for pairing stimuli for part 2 and the eye movements were not analyzed. After part 1 was finished, the faces of the same gender that received similar ratings were paired to form 60 pairs as the stimuli in part 2. In part 2, in each trial, each pair of faces was shown on the screen with one on the left and one on the right. Participants were required to indicate which face they preferred. There was no time limit. Participants could move their eyes freely to compare the two images. They were told to press a button to indicate which face (left or right) they preferred once they had made their decision. Eye movements were recorded using an Eyelink 1000 eye tracker. In data acquisition, fixation location information was extracted using Eyelink Data Viewer. Saccade motion threshold was 0.15 degree of visual angle; saccade acceleration threshold was 8000 degree/square second; saccade velocity threshold was 30 degree/second. These are the EyeLink defaults for cognitive research.

Example 7—Switching Hidden Markov Model

A standard hidden Markov model (HMM) contains a vector of prior values of the hidden states, a transition matrix of the hidden states, and a Gaussian emission for each hidden state. The prior values indicate the probabilities of the time-series data starting from the corresponding hidden states. The transition matrix indicates the transition probabilities between any two hidden states. The Gaussian emissions indicate the probabilistic associations between the observed time-series data and the hidden states. In the previous EMHMM approach (Chuk et al., 2014), the hidden states corresponded to the regions of interest (ROIs), the emissions were the eye fixation locations, and the emissions in an ROI were represented as a 2-D Gaussian distribution (see FIG. 1a).

In contrast to a standard HMM, a switching HMM (SHMM) contains two levels of hidden state sequences; the low-level hidden state sequence models the temporal pattern of the time-series data following a standard HMM, while the high-level hidden state sequences indicate the transitions between the HMM parameters used by the low-level hidden state sequence. Formally, $z_{n,t} \in \{1, \ldots, K\}$ are the low-level hidden states, and $s_{n,t} \in \{1, \ldots, S\}$ the high-level hidden states, and $x_{n,t}$ the observations, where n indexes the sequences and t indexes time. Both the high-level state sequence and the low-level state sequence are $1^{st}$-order Markov chains. The prior probability and transitions of the low-level hidden state depends on the current high-level state, $$p(s_n) = p(s_{n,1}) \Pi_{t=2}^{\tau_n} p(s_{n,t} | s_{n,t-1}) \tag{1}$$

$$p(z_n | s_n) = p(z_{n,1} | s_{n,1}) \Pi_{t=2}^{\tau_n} p(z_{n,t} | z_{n,t-1}, s_{n,t}), \tag{2}$$

where $\tau_n$ is the length of the n-th sequence. The high-level state sequence is parametrized by the prior vector $\rho$ and transition matrix B, $$p(s_{n,1}=j) = \rho_j, \; p(s_{n,t}=j | s_{n,t-1}=j) = b_{i,j}. \tag{3}$$

Given that the high-level state is $s_{n,t}=j$, the low-level state sequence is parametrized by the prior vector $\pi^{(j)}$ and transition matrix $A^{(j)}$, $$p(z_{n,1}=k | s_{n,1}=j) = \pi_k^{(j)}, \; p(z_{n,t}=k | z_{n,t-1}=k, s_{n,t}=j) = a_{k,k}^{(j)}. \tag{4}$$

The emission densities are Gaussians and depend only on the low-level hidden state (i.e., they are shared among high-level states), $$p(x^{n,t} | z_{n,t}=k) = N(x_{n,t} | \mu_k, \Lambda_k^{-1}), \tag{5}$$

where $\mu_k, \Lambda_k^{-1}$ are the mean vector and covariance matrix of the Gaussian. It was assumed that the number of low-level states for each high-level state is the same. The joint probability model for the SHMM is $$p(X,Z,S) = \Pi_{n=1}^{D} [p(s_{n,1}) p(z_{n,1} | s_{n,1}) p(x_{n,1} | z_{n,1}) \Pi_{t=2}^{\tau_n} p(s_{n,t} | s_{n,t-1}) p(z_{n,t} | z_{n,t-1}, s_{n,t}) p(x_{n,t} | z_{n,t})]. \tag{6}$$

In practice, the SHMM can be turned into a standard HMM by combining the high-level and the low-level hidden state variables into a single hidden state variable, whose values are the Cartesian product of the low- and high-level state values. Here, it was assumed that the low-level states were shared among the high-level states (S), and thus the number of low-level states (K) was the same for each high-level state. Consequently, the equivalent standard HMM had S*K augmented hidden states $\tilde{z}_{n,t}$. The augmented states took a value pair (j,k), where j indicates the high-level state and k indicates the low-level state. The transition probabilities and the prior values therefore were defined as, $$p(\tilde{z}_{n,t}=(j',k')|\tilde{z}_{n,t-1}=(j,k))=\tilde{a}_{(j,k),(j',k')}=b_{j,j'}a_{k,k'}^{(j')}, \quad (7)$$

$$p(\tilde{z}_{n,1}=(j,k))=\tilde{\pi}_{(j,k)}=\rho_j\pi_k^{(j)}. \quad (8)$$

Thus the relationship between the augmented hidden states and the two separate levels of hidden state sequences were defined as $$p(\tilde{z}_n)=p(z_n,s_n)=p(z_n|s_n)p(s_n)=p(z_{n,1}|s_{n,1})p(s_{n,1})\Pi_{t=2}^{\tau_n}p(z_{n,t}|z_{n,t-1},s_{n,t})p(s_{n,t}|s_{n,t-1})=p(s_{n,1},z_{n,1})\Pi_{t=2}^{\tau_n}p(s_{n,t},z_{n,t}|s_{n,t-1},z_{n,t-1}) \quad (9)$$

The transition matrix and the prior vector had block structures, $$\tilde{A} = \begin{bmatrix} b_{1,1}A^{(1)} & b_{1,1}A^{(2)} \\ b_{2,1}A^{(1)} & b_{2,2}A^{(2)} \end{bmatrix}, \quad (10)$$

$$\tilde{\pi} = \begin{bmatrix} \rho_1\pi^{(1)} \\ \rho_2\pi^{(2)} \end{bmatrix}. \quad (11)$$

Figure 6:
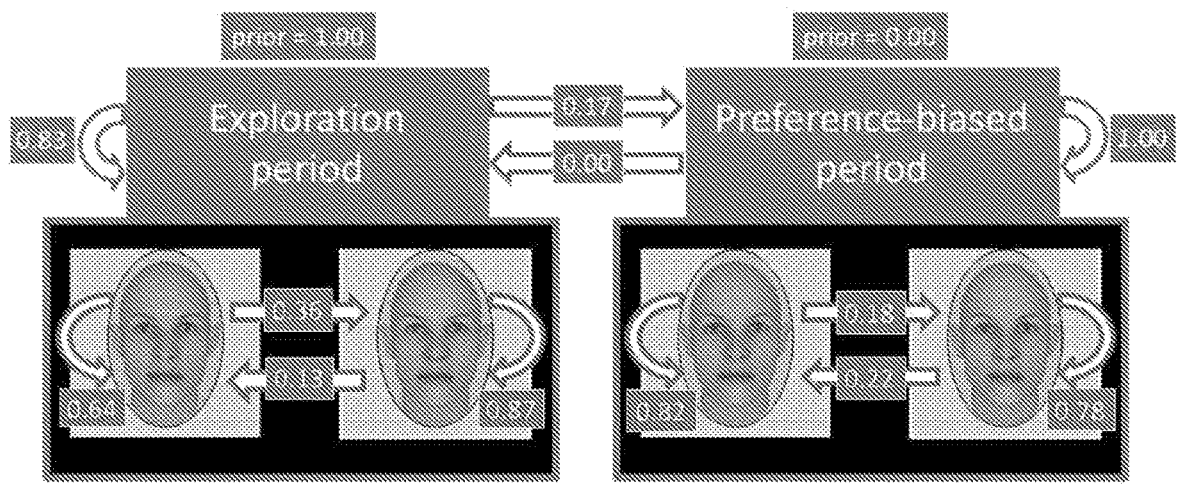
FIG. 6 shows an example SHMM model summarizing a participant's eye movement pattern in the preference decision-making task. The blue arrows indicate the transition probabilities between cognitive states (high-level states); the red arrows indicate the transition probabilities between the ROIs (low-level states).

In the implementation, the high-level hidden states represent the cognitive states, whereas the low-level hidden states correspond to ROIs over the stimuli. The high-level state sequence has its own transition matrix, which governs the transitions between cognitive states. The low-level states (ROIs) are shared among the high-level states. Taking the preference decision-making task as an example, it was assumed that participants have two cognitive states: an exploration period that involves information sampling without preference to a specific stimulus, and a preference-biased period where preference is formed and eye movement behavior can be influenced by the preference. A simplified decision process was assumed where a participant started in the exploration period, and that once the participant had sampled enough information in the exploration period, they transitioned to the preference-biased period and could not transition back to the exploration period. That is, once the preference-biased period was entered it could not be exited until the response decision. To examine a gaze cascade effect, that is a gaze bias towards the later-selected object (see, e.g., Shimojo et al. 2003), it was assumed that the low-level HMM had two ROIs, each corresponded to a stimulus for choice. FIG. 6 illustrates an example model summarizing a participant's eye movement pattern. As shown in the figure, the high-level HMM consisted of two cognitive states as its hidden states: exploration and preference-biased periods. The blue arrows indicate the transitions between the two states, and the numbers indicate transition probabilities. Eye movements within each state were modeled with a low-level HMI, whose hidden states represent ROIs of eye movements. The red arrows represent transitions between ROIs. The two cognitive states have the same ROIs but different transition probabilities.

Example 8—Training Individual SHMMs

An Expectation-Maximization (EM) algorithm was performed to estimate the SHMM parameters. In the Expectation step (E-step), the responsibilities were calculated using the standard forward-backward algorithm with the block transition matrix, initial state vector, and emission densities. In the Maximization step (M-step), the prior and pairwise responsibilities were summed over the high-level and the low-level states, respectively, to yield the parameter updates for both the high-level states and the low-level states.

For example, the prior responsibilities were summed over the low-level hidden states for each of the high-level state to yield the parameter updates for the low-level state sequence, and then they were summed over the high-level states to yield the parameter updates for the high-level state sequence. Similarly, the pairwise responsibilities were summed over the low-level hidden states for each high-level state to yield the updates for each low-level transition, and then were summed over the high-level hidden states to yield the updates for the switching (transition) matrix of the high-level state sequence.

For each participant, two SHMMs were trained; one using the data from the left-selected trials and one using the data from the right-selected trials. The two SHMMs were combined into one for each individual as follows. Preliminary analysis indicated that the exploration periods of the left-selected and right-selected trials were similar. In other words, the eye movements during exploration periods were consistent regardless of which side was selected. Thus, the transition matrices for the exploration period of the left-selected and right-selected models were directly averaged together. For the preference-biased period, the two preferred-side parameters and the two non-preferred-side parameters were averaged, essentially normalizing the right-selected trials into left-selected trials. In order to focus the analyses on the transition between the stimuli during preference decision making, only two Gaussian emissions were used per model, one on each side, for the low-level states (FIG. 6). For SHMM estimation, one Gaussian centered over each stimulus was initialized, with covariance that covered the stimulus. Thus, it could be considered here that the low-level states of the model were pre-specified (and thus not hidden), since it could be determined with good confidence which stimulus was viewed. The advantage of using Gaussian rather than discrete emissions is that it can be easily extended to analyses that explore more ROIs (i.e., more hidden lower-level states) on each stimulus. Two high-level hidden states were used to reflect that the participants would transition from the exploration period to the preference-biased period during a trial.

For SHMM estimation, the transition matrices of the high-level state were initialized as [0.95, 0.05; 0.0, 1.0] and high-level prior as [1.0, 0.0], which encodes the assumed behavior of starting in the exploration period and staying there (0.95), and then eventually transitioning to the preference-biased period (0.05) and not back (0.00). During training, this initialization causes the probability of transitioning from the preference-biased to the exploration period to stay at 0 (since all potential sequences that transition from the preference-biased to the exploration period are given probability zero). The transition matrices of the low-level states were initialized as uniform distributions. After the initialization, the Gaussian ROIs and transition probabilities were updated in the EM algorithm.

Example 9—Clustering to Discover Common Patterns

To examine the general eye movement pattern adopted by all individuals during the exploration period, an HMI was created using the exploration transition matrix and Gaussian emissions for each individual, and these HMIs were clustered or summarized into one group using the Variational Hierarchical Expectation Maximization (VHEM) algorithm (see, e.g., Coviello et al., 2014). The VHEM algorithm clusters HMIs into a predefined number of groups according to their probability distributions and characterizes each group using a representative HMM. A similar procedure was performed to obtain the general eye movement pattern for the preference-biased period.

To examine individual differences in decision making behavior, the participants' high-level transition matrices were clustered into 2 groups using the k-means clustering algorithm (see, e.g., MacQueen, 1967). The aim was to discover differences in the high-level cognitive behavior involving the explorative and preference-biased periods. For each group, representative exploration-period and preference-biased-period HMIs were computed by running the VHEM algorithm on the exploration-period and preference-biased-period HMMs of that group respectively[1]. It was then examined how participants in the two groups differed in decision making behavior, including their differences in the gaze cascade plot/effect, transition between the exploration and preference-biased periods, distribution of number of fixations in exploration/preference-biased periods, and accuracy of inferring preference choices from eye movement data.

[1] Since the differences in the transitions between the two sides were of interest, all HMMs in this example were forced to use the same set of ROIs that covered each face.

Example 10—Transition Between Exploration and Preference-Biased Periods

After participants' high-level transition matrices were clustered into two groups, it was further investigated how the participants in these two groups differed in decision-making behavior. More specifically, the probability that the participant was in the preference-biased period was investigated from the beginning to the end of a trial. For each trial, the posterior probabilities of all possible high-level state sequences were computed given the observed eye gaze data. Then a sequence of probabilities of being in the preference-biased period was computed by computing the expectation over the high-level state sequences, i.e., by computing the weighted average over all high-level state sequences where the weights are the posterior probabilities. This was performed on all trials in all participants. Since the duration differed in each trial, to examine the proportion of time a participant spent in the exploration and preference-biased periods relative to the whole trial, the different durations were normalized across the trials by dividing each trial into the same number of segments (21 in the instant experiments). Then, for each segment in a trial, the probability of time that the participant was in the preference-biased period was calculated. For each participant, the mean probability was calculated across all trials for each segment. Finally, the means across participants in the same group were averaged and the mean probability at each trial segment was plotted for the two participant groups separately. The plot represented the percentage of time at each trial segment the participants were in the preference-biased period. This examination allowed the detection of the difference in temporal dynamics of cognitive state changes in a trial between groups.

The number of fixations in the exploration and preference-biased period between the two groups were also examined. To this end, for each trial and each participant, the posterior probabilities of all high-level state sequences were computed, and then the numbers of fixations in the exploration and preference-biased periods counted. The aggregated probabilities over all trials and all high-level sequences were then used to form a probability distribution of number of fixations in each high-level state for a participant. The participants' probability distributions were then averaged together in each group.

Example 11—Inferences of Individual Preferences

It was examined whether SHMMs could be used to infer an individual's preference choice in a trial. For each participant, the trials in the preference decision making task were split into two sets: one for the trials in which the left-side image was chosen to be preferred, and the other for the trials in which the right-side image was chosen. Similar to the preference decision making task, face images used in a trial were matched in gender and attractiveness ratings. Thus, the two sides were expected to be chosen equally often. For each set, all but one trial was used to train a left-selected and a right-selected SHMM and the held-out trial was used for testing. For testing, an aggregated SHMM was created from the two trained SHMMs, which could be used to infer the participant's choice. In particular, the aggregated SHMM contained 3 high-level states: exploration, left-selected preference-biased, and right-selected preference-biased periods. In the high-level transition matrix of this aggregated SHMM, the transition probability of moving from the exploration period to a preference-biased period was equally divided between the left-selected and right-selected preference-biased periods. Finally, to perform inference of the participant's choice on the test eye fixation sequence, the posterior probability of high-level state of the last fixation $p(s_T|x_1, \ldots, x_T)$ given the test sequence $(x_1, \ldots, x_T)$ was computed, which indicates the probability of being in either the left-selected or right-selected preference-biased period at the end of the trial. The left/right-selected preference-biased period with higher probability was predicted as the choice. This was repeated over all trials for each participant to calculate the inference accuracy.

The inferences were performed in three ways. First, to examine the percentage of fixations in a trial required for making above-chance-level inferences, the first 10% of the fixations were used for the inferences and this proportion was increased by 5% each time until all fixations (100%) were used. The inference task was therefore conducted 19 times, and the mean inference accuracy was calculated each time. Second, to examine how quickly a decision could be inferred, inference on increasing duration of fixation sequences was performed from the beginning of the trial (e.g., the fixations in the first 1 second, the fixations in the first 2 seconds, etc.). Third, the gaze cascade model suggested that although preferences were shaped during a trial when participants switched their fixations between the two stimuli, the fixations immediately before the end of the trial were usually significantly biased to the preferred stimulus. Thus, these fixations should be better predictors for participants' preference than the earlier fixations. Accordingly, in a separate examination only the fixations in the last 2 seconds before the decision were used to perform the inferences.

Example 12—Categorization of Individual SHMMs

One SHMM was trained for each participant and 1) a standard HMM using the exploration period transition matrix to represent the participant's eye movement pattern during the exploration period and 2) a standard HMM using the preference-biased period transition matrix to represent the participant's eye movement pattern during the preference-biased period were created.

Table 2 below shows the average high-level state transition matrix. Participants started in the exploration period, and had a 55% probability to remain in the exploration period. Otherwise there was 45% probability to transition to the preference-biased period, and remained there until the end of the trial.

TABLE 2

High-level state transition matrix of all subjects.

|  | Exploration | Preference |
|---|---|---|
| Prior | 1.00 | 0.00 |
| Exploration | 0.55 | 0.45 |
| Preference | 0.00 | 1.00 |

Next, the exploration period HMMs of the 24 participants were clustered into one representative HMM using the VHEM algorithm. Tables 3a and 3b below show the transition matrices of the representative exploration period HMM and preference-biased HMM, respectively.

TABLE 3a

The transition matrix of the representative Exploration HMM obtained by clustering the 24 exploration period HMMs into one group.

|  | Left | Right |
|---|---|---|
| Prior | 0.70 | 0.30 |
| Left | 0.64 | 0.36 |
| Right | 0.12 | 0.88 |

TABLE 3b

The transition matrix of the representative preference-biased HMM obtained by clustering the 24 preference-biased period HMMs into one group

|  | to Chosen | to Not-chosen |
|---|---|---|
| Prior | 0.53 | 0.47 |
| from Chosen | 0.77 | 0.23 |
| from Not-chosen | 0.33 | 0.67 |

As indicated in Table 3a above, participants tended to first view the left side with several fixations, and then transition to view the right side for several fixations. After viewing the right side, the participants rarely looked back at the left side (12% probability). This suggested that participants performed a quick scan of the two sides during the exploration period.

Similarly, Table 3b above shows that participants in the preference-biased period were biased to remain looking at the to-be-chosen side (77%) more often than to the not-chosen side (67%); furthermore, they were more likely to transition from the not-chosen-side to the chosen side (33%), than vice-versa (23%).

To investigate individual differences in the gaze cascade effect, participants were clustered based on their high-level transition matrices into two groups. It was found that one group (group A) included 11 participants and the other (group B) included 13 participants. Table 4 and Tables 5a and 5b below show the high-level transition matrices, and the transition matrices of the representative exploration and preference-biased period HMMs for the two groups.

TABLE 4

Transitions matrices of the high-level states of Group A (11 participants) and Group B (13 participants).

|  | Exploration | Preference |
|---|---|---|
| Group A |  |  |
| Prior | 1.00 | 0.00 |
| Exploration | 0.68 | 0.32 |
| Preference | 0.00 | 1.00 |
| Group B |  |  |
| Prior | 1.00 | 0.00 |
| Exploration | 0.45 | 0.55 |
| Preference | 0.00 | 1.00 |

TABLE 5a

Transition matrices of the representative exploration period of Group A (11 participants) and Group B (13 participants).

|  | Left | Right |
|---|---|---|
| Group A |  |  |
| Prior | 0.76 | 0.24 |
| Left | 0.67 | 0.33 |
| Right | 0.17 | 0.83 |
| Group B |  |  |
| Prior | 0.64 | 0.36 |
| Left | 0.60 | 0.40 |
| Right | 0.09 | 0.91 |

TABLE 5b

Transition matrices of the representative preference-biased period of Group A (11 participants) and Group B (13 participants).

|  | Chosen | Not-chosen |
|---|---|---|
| Group A |  |  |
| Prior | 0.50 | 0.50 |
| Chosen | 0.83 | 0.17 |
| Not-chosen | 0.25 | 0.75 |
| Group B |  |  |
| Prior | 0.54 | 0.46 |
| Chosen | 0.71 | 0.29 |
| Not-chosen | 0.39 | 0.61 |

From the high-level state transition matrix, group A had higher probability to stay in the exploration period (68%) than group B (45%). Thus, the exploration period of group A was longer than that of group B. By examining the transition matrix during the exploration period, it was found that group A had a stronger tendency to start exploring from the left side (76%) than group B (64%) and had a higher probability to stay looking at the left side (67%) than group B (60%). After switching to the right side, group A also had higher probability to transition back to the left side (17% vs 9%).

During the preference-biased period, participants in group A showed an apparent fixation bias to stay looking at the chosen side. More specifically, participants in group A had a stronger tendency to keep looking at the to-be-chosen side (83%) than group B (71%) and switched less often between the two sides than group B.

Example 13—Cascade Plot

Figure 7:
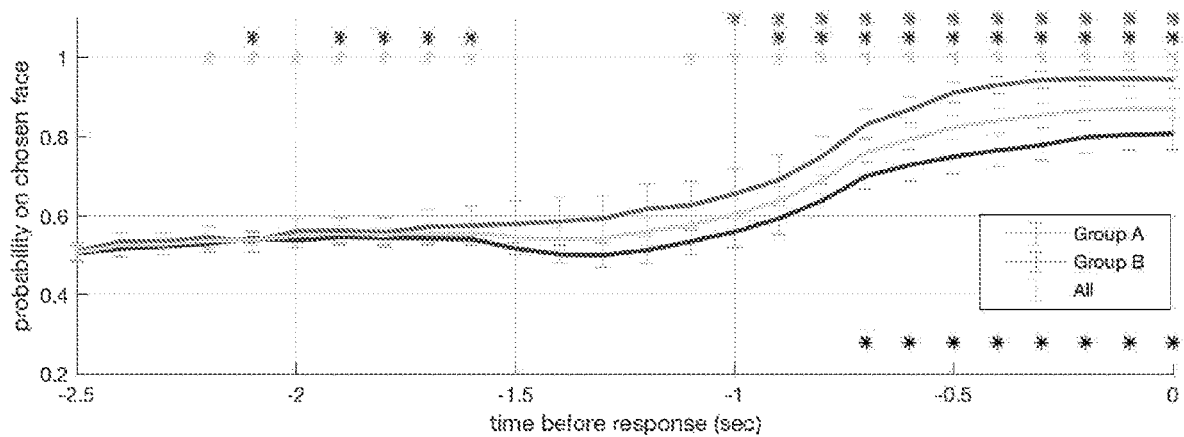
FIG. 7 shows the gaze cascade plots during the last 2.5 seconds before response for two participant groups (Group A and B) and all participants (All). The red, blue, and green stars on the top indicate the time points at which the gaze cascade effect occurred; the black stars on the bottom indicate the time points during which the two groups had significant differences in the proportion of time spent on the chosen item.

The analyses showed that participants were biased to look more at the side that they were about to choose during the preference-biased period. However, the clustering results showed that this difference was more obvious for one group of participants (group A) than the other group (group B). To visualize the difference in the gaze cascade effect between the two participant groups, a gaze cascade plot was generated. The plot showed the probability that participants looked at the image to be chosen during the last 2.5 seconds prior to the response. FIG. 7 shows the gaze cascade plots of the two groups and their average.

As depicted in the "All" plot in FIG. 7, participants spent more time on inspecting the side that they were about to choose near the end of a trial. The proportion of time spent on the chosen side went from chance level 0.5 steadily up until it reached around 0.87. The probability that each participant looked at the chosen stimuli at each time point was estimated at a 100-millisecond (ms) interval. To test the hypothesis that across the time intervals there was significant difference in the probability of looking at the chosen side, and that the two groups of participants differed in the time interval effect, a mixed AVOVA was performed on the probability of looking at the chosen side with time interval as a within-subject variable and group as a between-subject variable. The results showed a significant main effect of time interval, $F(3.043, 66.938)=52.163$, $p<0.001$, $\eta_p^2=0.703$, a significant main effect of group, $F(1, 22)=5.481$, $p=0.029$, $\eta_p^2=0.199$, and a marginal interaction between time interval and group, $F(3.043, 66.938)=2.307$, $p=0.084$, $\eta_p^2=0.095^2$. In addition, there was a significant linear trend, $F(1, 22)=126.657$, $p<0.001$, $\eta_p^2=0.852$, and quadratic trend, $F(1, 22)=19.609$, $p<0.001$, $\eta_p^2=0.471$, across time intervals. These results demonstrated that during the last 2.5 seconds before response, participants had a significant increase in probability of looking at the chosen side. In addition, group A had higher a probability of looking at the chosen side than group B, indicating a stronger cascade effect.

[2] Greenhouse-Geisser correction was applied whenever the assumption of sphericity was not met.

Post-hoc t-test showed that participants started to look at the chosen item significantly above chance level at around 1100 ms before the end of the trial (i.e., the beginning of the gaze cascade effect), $t(23)=2.27$, $p=0.033$, $d=0.46$ (Here d refers to Cohen's d, an effect size measure to indicate standardized difference between two means), until the end of the trial. Within this time period, the probability to look at the chosen face rose from 58% to 87%. Furthermore, there was a short period from 2200 ms and 1600 ms before the end of the trial, where the participants also looked at the chosen side with slightly higher probability than chance level according to t-test (~55%; FIG. 7).

The plots of the two participant groups showed some interesting differences. The participants in group A showed a stronger gaze cascade effect. The probability that group A looked at the chosen item reached 94.5% at the end. A t-test was conducted to examine when their probability of viewing the chosen stimulus was above chance level. The result showed that this occurred at around 1000 ms before the end of a trial, $t(10)=2.44$, $p=0.035$, $d=0.74$, at which time point they spent about 66% of their time on the chosen item. In contrast, participants in group B had a weaker cascade effect, looking at the chosen item about 81% of the time at the end. A t-test indicated that the proportion of time spent on the chosen item was significantly above the chance level at 900 ms before the end of a trial, $t(12)=2.29$, $p=0.041$, $d=0.64$, at which point the probability to view the chosen side increased from 59% to 81%. Group B also exhibited a short period of slightly higher than chance viewing (54%) of the chosen side between 2100 ms and 1600 ms before the end of the trial (FIG. 7). The proportions at each time point were also compared between the two groups using independent sample t-tests. It was found that during 700 ms before the end of a trial to the end of the trial, group A spent significantly more time looking at the to-be-chosen item than group B (FIG. 7). Thus, although both groups exhibited the gaze cascade effect, they differed in both magnitude and onset time, suggesting substantial individual differences in the gaze cascade effect. These results indicated that the EMSHMM method of the instant invention allowed the detection of these individual differences in the gaze cascade effect through clustering participants' eye movement patterns according to their similarities.

In addition, with the HMM based approach the similarity of each participant's eye movement pattern during the preference-biased period to the representative pattern of group A or group B could be quantitatively assessed by calculating the log likelihood of the participant's eye movement pattern being generated by the representative model. To quantify a participant's eye movement pattern along the continuum between the representative patterns of group A and group B, the A-B scale was defined as $(LA-LB)/(|LA|+|LB|)$, where LA is the log likelihood of the eye movement pattern being generated by the group A model, and LB is the log likelihood of the eye movement pattern being generated by the group B model (Chan et al., 2018). The larger the A-B scale, the more similar the pattern is to the representative pattern of group A, and vice versa for the representative pattern of group B. Among the participants, a significant positive correlation was observed between A-B scale and gaze cascade effect as measured by the average probability looking at the chosen item from the onset of the effect (1000 ms prior to the response) to the end ($r=0.50$, $p=0.012$). In other words, the more similar participants' eye movement patterns during the preference-biased period to the representative pattern of group A, the stronger their gaze cascade effects.

Example 14—Transition Between Exploration and Preference-Biased Periods

Figure 8A:
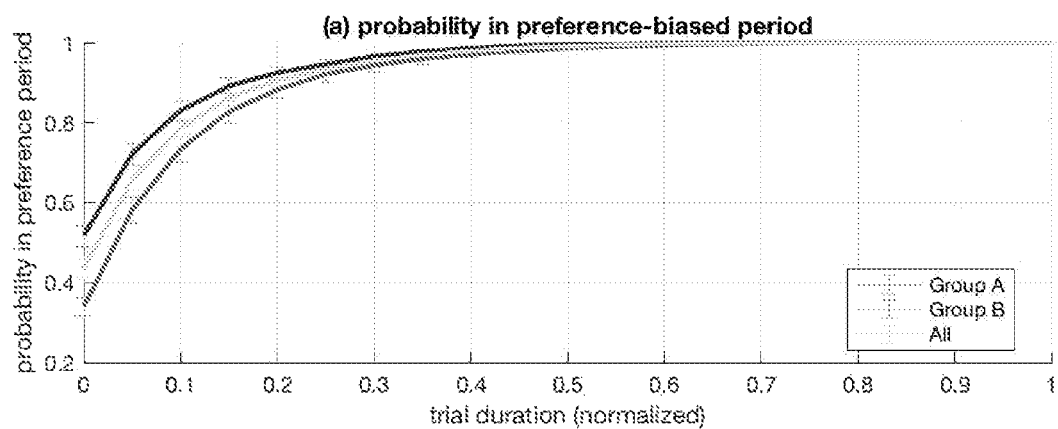
FIGS. 8A-B show the differences in transitions between exploration and preference-biased periods between two participant groups.
Figure 8B:
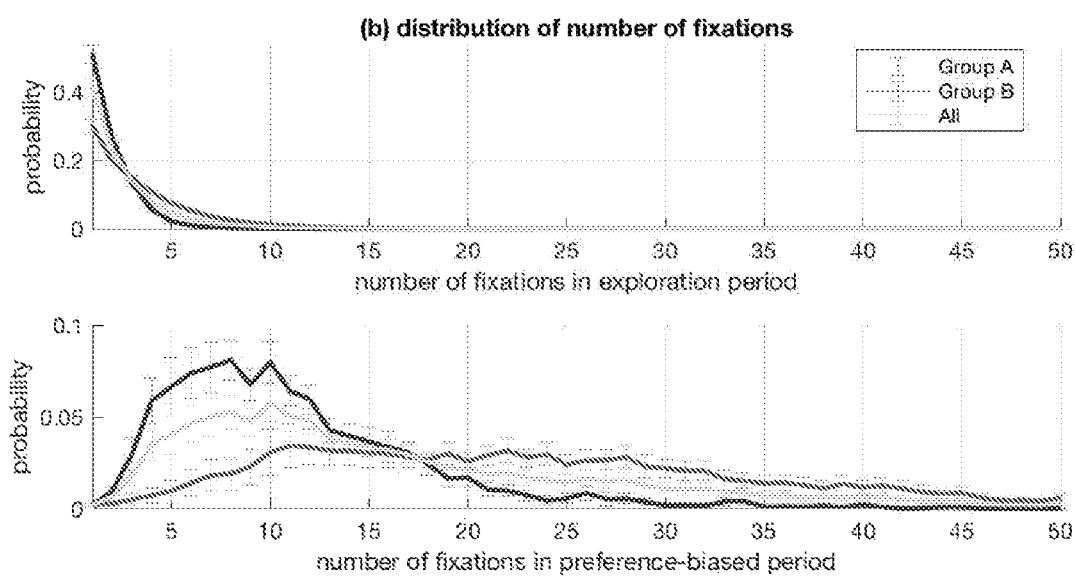

To examine whether the two participant groups differed in their transition behavior between the two cognitive states throughout a trial, the trial duration was normalized by dividing each trial into 21 time segments and for each participant the percentage of trials, or the frequency that the participant was in the preference-biased period during each time segment was examined. FIG. 8A shows the average probability of the two groups being in the preference-biased period throughout a trial. FIG. 8B shows the probability distribution of number of fixations in the exploration period, and number of fixations in the preference-biased period. The vertical bars indicate standard errors.

The results showed that for both groups, the probability of being in the preference-biased period increased soon after a trial began. To test the hypothesis that group A and group B had different probabilities across the time segments, a mixed ANOVA on probability of being in the preference-biased period with time segment as the within-subject variable and group as the between-subject variable was conducted. The results showed a significant time segment effect, $F(1.384, 30.445)=339.091$, $p<0.001$, $\eta_p^2=0.939$, a significant group effect, $F(1, 22)=7.770$, $p=0.011$, and a significant interaction between group and time segment, $F(1.384, 30.445)=10.064$, $p=0.001$, $\eta_p^2=0.314$. These results indicated that in general group B had higher probability to be in preference-biased period than group A, especially in the beginning time segments of a trial (FIG. 8A). Although group A entered the preference-biased period later, group A had a stronger gaze cascade effect. In contrast, group B entered the preference-biased period earlier, but had a weaker gaze cascade effect.

A t-test was used to test the hypothesis that group A and group B differed in average number of fixations per trial. It was found that group A (M=29.0) had a significantly larger average number of fixations in a trial than group B (M=13.3), $t(22)=4.44$, $p<0.001$, $d=1.75$. Group A also had a larger average number of fixations in the exploration period (group A: M=3.38; group B: M=1.88), $t(22)=8.46$, $p<0.001$, $d=3.37$, and in the preference-biased state (group A: M=25.61; group B: M=11.5), $t(22)=4.10$, $p<0.001$, $d=1.62$ (FIG. 8B). However, after normalizing for the total number of fixations, group A (M=0.147) and group B (M=0.173) did not differ in the fraction of fixations in the exploration or preference-biased period, $t(22)=-1.11$; $p=0.28$; $d=0.45$.

Further, the hypothesis was tested that group A and group B differed in the number of eye gaze switches between stimuli during a trial. Group A (M=5.66) had more switches than group B (M=4.10) on average, $t(22)=2.81$, $p=0.01$, $d=1.12$. However, this effect was mainly due to group A having more fixations in a trial in general. After normalizing for the total number of fixations in a trial, group A (M=0.211) had a smaller fraction of eye fixations that involved switching between stimuli than group B (M=0.328), $t(22)=-7.20$, $p<0.001$, $d=2.97$. This effect suggested that group A tended to explore a stimulus longer before switching to the other stimulus than group B. Note that since the clustering was only based on participants' cognitive (high-level) state transitions, these differences in number of fixations per trial and frequency of switch between stimuli emerged naturally as a result of the clustering.

Example 15—Inference of Participants' Preference Choices

Figure 9A:
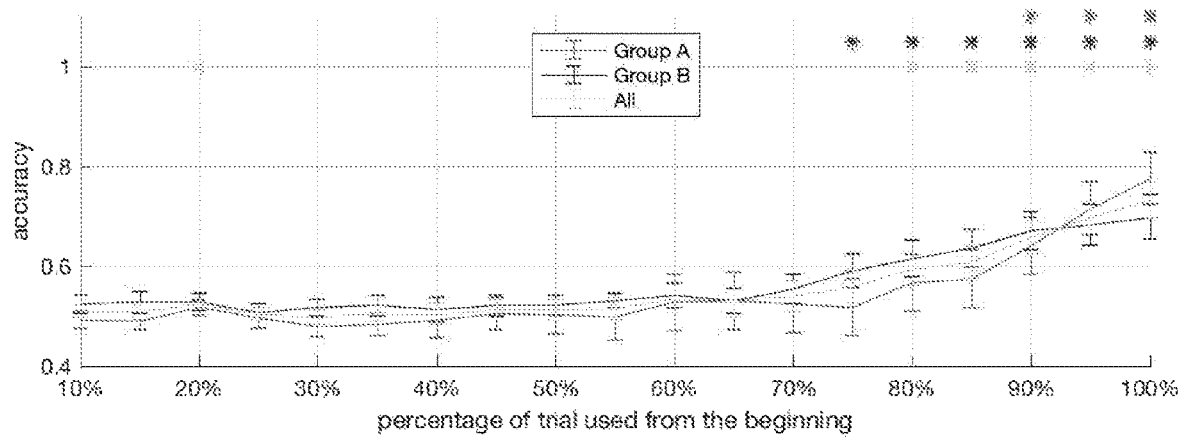
FIGS. 9A-B show the average inference accuracies of the two participant groups.
Figure 9B:
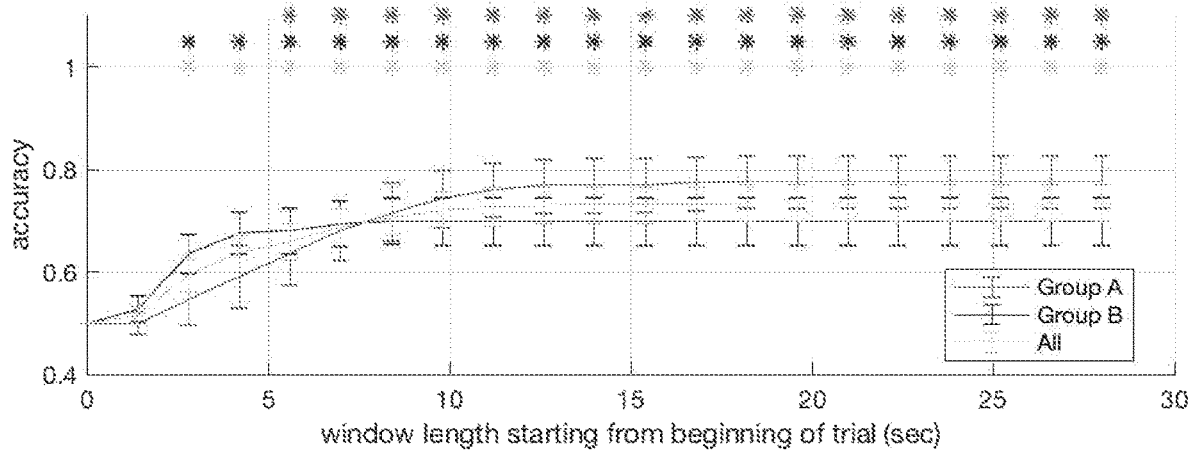

It was also explored whether the models could be used to infer an individual's preference choice in each trial given partial eye movement data. The fixations from the first 10% of the trial according to normalized duration ere used and were gradually increased at a step of 5%. FIG. 9A shows the average inference accuracies of the two groups using partial fixations in a trial, selected as a percentage of each trial's duration from the beginning. FIG. 9B shows the average inference accuracies of the two groups using different window lengths starting from the beginning of the trial (note that participants had different trial lengths, with the average length 5.65±2.57 seconds; Group A had average trial length of 7.67±2.32 seconds, while Group B had average trial length of 3.93±1.13 seconds). The red, blue, and green stars on the top indicated the data points at which the accuracy was significantly higher than the chance level based on t-test, for each group and all participants respectively.

As shown in FIG. 9A, when using the first 75% to 90% of the fixations in a trial, the average inference accuracy was higher for group B than for group A. In contrast, when the first 95% or all fixations of a trial were used, the inference accuracy for group A was higher than that for group B. To test the hypothesis that group B had higher inference accuracy when 75% to 90% of the fixations were used whereas group A had higher inference accuracy when 95% to 100% of fixations were used, a mixed ANOVA on inference accuracy was conducted with amount of fixations (75% to 100% at a step of 5%) as the within-subject variable and group as the between-subject variable. The results showed a main effect of amount of fixations, $F(1.356, 29.840)=30.778$, $p<0.001$, $\eta_p^2=0.583$, and an interaction between amount of fixations and group, $F(1.356, 29.840)=5.657$, $p=0.016$, $\eta_p^2=0.205$. The main effect of group was not significant, $F(1, 22)=0.077$, n.s. These results indicated that, as shown in FIG. 9A, group B had higher inference accuracy when a smaller amount of fixations were used (75% to 90%), whereas group A had higher inference accuracy when a larger amount of fixations were used. When the inference accuracies were compared against the chance-level (0.5) using t-test, it was found that when using the first 75% to 85% of the fixations, group B's inference accuracy was significantly above the chance-level, whereas group A's inference accuracy was not. When using the first 90% to 100% of the fixations, inference accuracy was significantly above the chance-level for both groups (FIG. 9A). In other words, participants in group B revealed their biases to the preferred stimulus earlier than group A.

To examine the actual time when a group's accuracy became significantly above chance, FIG. 9B plots the average inference accuracy using time windows (in seconds) starting from the beginning of the trial. After the start of the trial, Group B's inference accuracy increased more rapidly than Group A, and became significantly above chance at around 3 seconds, and then saturated at around 4 seconds. In contrast, Group A's inference accuracy increased slowly, became above chance-level at around 6 seconds, and saturated at around 10 seconds. Although Group A's accuracy increased more slowly, it saturated at a higher value than Group B.

Example 16—Last 2 Seconds Before Response

Figure 10A:
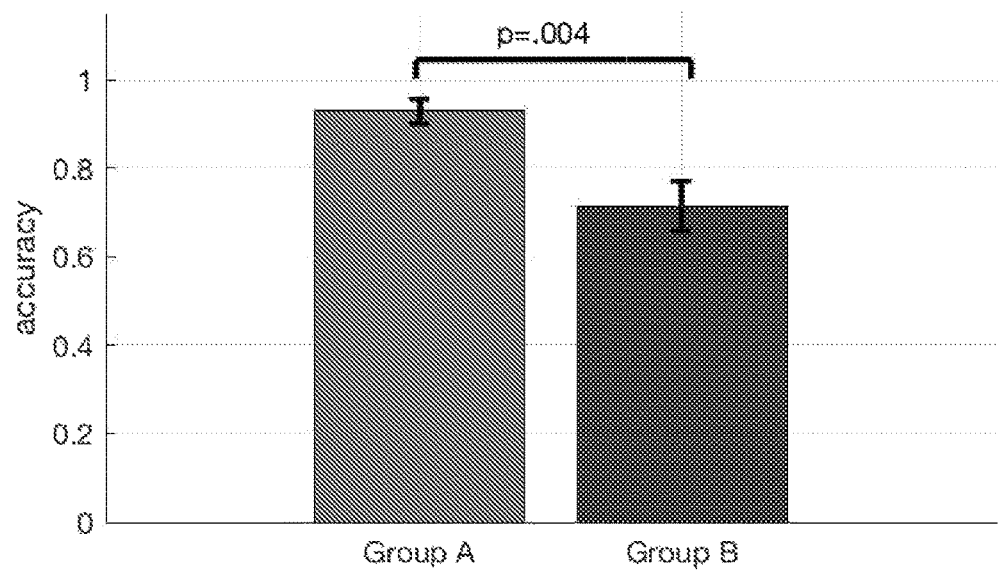
FIGS. 10A-B show the average inference accuracies using different fixation patterns.
Figure 10B:
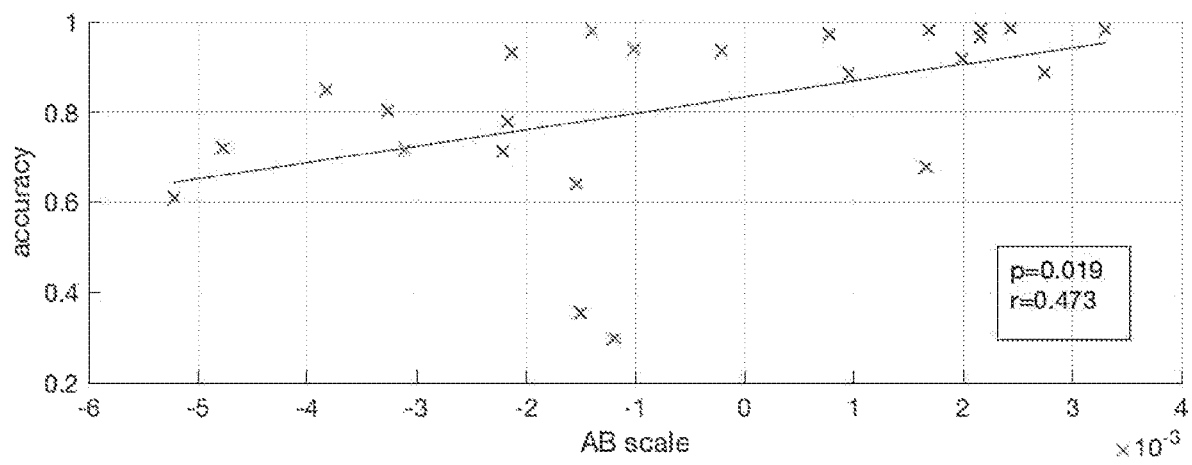

The gaze cascade effect suggested that eye movement patterns immediately before a preference decision response may provide a strong cue for inferring the preference. According to FIG. 7, participants started to show a tendency of looking at the chosen side more often at around 2 seconds before response. Thus, the accuracy of inferring participants' preferences was examined using the fixations during the last 2 seconds before the response. FIG. 10A shows the average inference accuracies of the two groups using fixations in the last 2 seconds until the response. FIG. 10B shows the more similar participants' eye movement patterns to the representative pattern of group A (i.e. the further to the right of the X-axis), the higher the inference accuracy.

First, the hypothesis was tested that for participants in both group A and group B, the average accuracy of inferring their preference decisions using the final 2 seconds was significantly above the chance level, and results supported this hypothesis (FIG. 10A): group A, M=0.93, $t(10)=15.89$, $p<0.001$, $d=4.79$; group B, M=0.71, $t(12)=3.79$, $p=0.003$, $d=1.05$. In addition, the hypothesis was tested that the inference accuracy of group A was significantly higher than that of group B. The result supported the hypothesis, $t(22)=3.26$, $p=0.004$, $d=1.33$. In addition, the more similar participants' eye movement patterns during the preference biased period to the representative pattern of group A, as opposed to that of group B (as measured in A-B scale), the higher the inference accuracy ($r=0.47$, $p=0.02$; FIG. 10B). This result was consistent with the observation that group A exhibited a stronger gaze cascade effect (FIG. 7). The clustering of the two groups was completely based on the eye movement data alone, and thus the group difference in inference accuracy emerged naturally as the result of the clustering.

Figure 11:
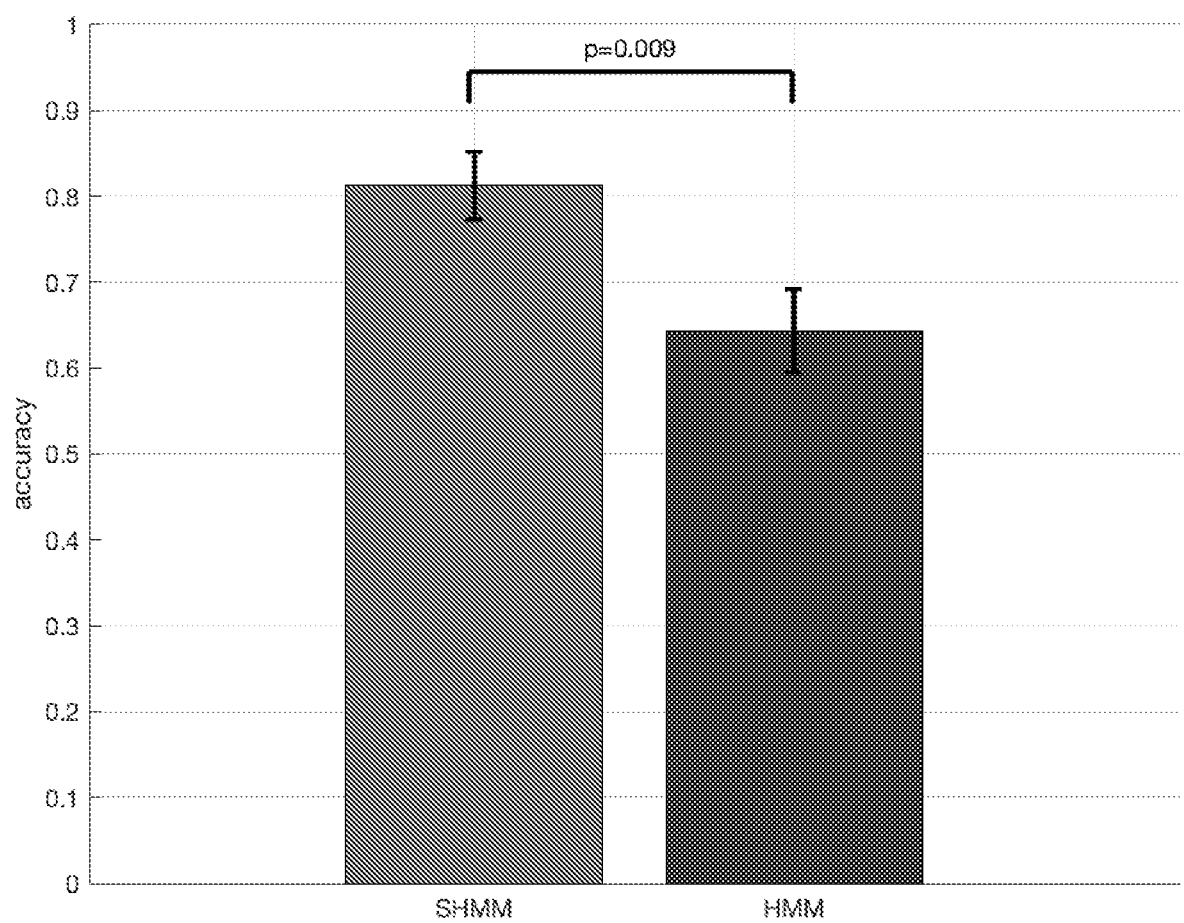
FIG. 11 shows the average inference accuracy using SHMMs and regular HMMs when using the last 2 seconds of the trials.

It was also tested whether a regular HMM without inferring participants' cognitive state transition, such as that used in the previous EMHMM approach (Chuk et al., 2014), would be able to reveal participants' preference choices. To this end, the same inference task was performed using regular HMMs in the EMHMM approach. As shown in FIG. 11, the average inference accuracy of SHMMs ($M=0.81$) was higher than HMMs ($M=0.64$) for all subjects, $t(46)=2.71$, $p=0.009$, $d=0.78$. A two-way ANOVA on inference accuracy was conducted with group and model (SHMM/HMM) as the independent variables. The results showed a significant main effect of group, $F(1, 44)=5.04$, $p=0.03$, $\eta_p^2=0.096$ and a significant main effect of model, $F(1, 44)=8.75$, $p=0.005$, $\eta_p^2=0.166$. There was no interaction between group and model, $F(1, 44)=1.91$, $p=0.17$. This result demonstrated again the advantage of EMSHMM for modeling eye movement patterns in tasks that involve cognitive state changes. FIG. 11 shows the average inference accuracy for all participants using SHMMs and regular HMMs when using the last 2 seconds of the trials.

Example 17—Relevance of the Study Results

The instant invention presents a novel method, EMSHMM, for modeling eye movement patterns in tasks that involve cognitive state changes. Similar to the previous hidden Markov modeling approach to eye movement data analysis EMHMM, the EMSHMM approach has several advantages over traditional eye movement data analysis methods such as ROI or fixation heat map analysis, including the ability to account for individual differences in both spatial and temporal dimensions of eye movements (i.e., through discovering personalized ROIs and transition probabilities among the ROIs) and to quantitatively assess these differences. In contrast to EMHMM, which uses a single regular HMM to model eye movements and assumes a participant's strategy is consistent throughout a trial, the EMSHMM approach uses multiple low-level HMMs corresponding to different strategies/cognitive states, and a higher-level state sequence to capture the transitions among different strategies/cognitive states. Thus, it is especially suitable for analyzing eye movement data in complex tasks that involve cognitive state changes such as decision-making tasks.

To demonstrate the advantages of using the EMSHMM approach, a preference decision-making task was conducted, in which participants viewed two faces with similar attractiveness ratings and decided which one they preferred. Previously two different eye movement patterns at different states of a trial had been observed; they usually began with exploring both alternatives and then focused on the one preferred by the end of the trial and these two eye movement patterns were associated with different cognitive states. In the instant EMSHMM approach, it was assumed that the two eye movement patterns were associated with two cognitive states, exploration period and preference-biased period, respectively. A switching HMM (SHMM) was used to summarize a participant's eye movement pattern in the preference decision-making task. The SHMM contained two ROIs that corresponded to the two faces of choice; two low-level HMMs that summarized the eye movement patterns during the exploration and preference-biased periods, respectively; and a high-level state sequence that captured the transitions between the two cognitive states.

A summary of all participants' high-level/cognitive state transitions showed that on average they had a 55% probability to remain in the exploration period, and 45% probability to transition to the preference-biased period, and remained there until the end of the trial (Table 2). When all participants' exploration period HMMs were summarized in one representative model, it was found that participants had a bias to start from looking at the stimulus on the left side and remain exploring there, and then switch to the right side (Table 3a). In contrast, when all participants' preference-biased period HMMs were summarized in one representative model, it was found that participants looked more often at the to-be-chosen, preferred stimulus (Table 3b). When the percentage of time that participants were looking at the to-be-chosen stimulus before the end of a trial was plotted, it showed a steady increase at about 1.5 seconds before the end, demonstrating a gaze cascade effect (FIG. 7).

When participants' SHMMs were clustered into two groups according to their cognitive state transitions, one group (group A) showed a stronger and earlier gaze cascade effect than the other group (group B; FIG. 7). The two groups also showed interesting differences in the temporal dynamics of eye movement patterns throughout a trial. More specifically, participants in group A entered the preference-biased period later than group B (FIG. 8A) but had a stronger cascade effect. In addition, group A's preference over the two alternatives could not be inferred with above-chance performance using early fixations of a trial until the first 90% of the fixations were used. In contrast, group B's preference could be inferred with above-chance performance with only the first 75% of the fixations (FIG. 9A). However, when only the fixations during the final 2 seconds before the decision response were used, group A's preference was inferred with a higher accuracy than group B. This phenomenon showed that although participants in group A revealed their preference in the eye movement patterns later in a trial than group B, their eye movement patterns contained more information for inferring their preferences. Recent research has suggested that indecisiveness, or decisional procrastination, is associated with informational tunnel vision: indecisive individuals tend to gather more information about the item that is eventually chosen while ignoring information about other alternatives. Accordingly, in the instant study participants in group B have exhibited a more 'indecisive' eye movement pattern than group A, since they entered the preference-biased period earlier, spent proportionally less time in the exploration period, and switched more frequently between the two stimuli for choice, which may be characteristics of informational tunnel vision. Thus, there exists a relationship between eye movement pattern similarity (as assessed using the EMHMM/EMSHMM approach) to the representative pattern of group B and participants' personality measures related to indecisiveness.

These individual differences in eye movement pattern and cognitive style during decision making have not been reported before in the literature. More specifically, previous studies only observed that decisions were related to the final fixations in a trial as revealed in the gaze cascade effect. However, using the instant method it can be shown that participants' preference can be inferred significantly earlier than the exhibition of the gaze cascade effect, and for some participants (e.g., group B) this inference could achieve above-chance level performance with only the first 75% of the fixations. Interestingly, these participants also tended to show a weaker gaze cascade effect. These findings demonstrate the importance of taking individual differences into account in the understanding of human decision-making behavior. Importantly, while regular HMMs without cognitive state transitions in an EMHMM approach could also account for individual differences in eye movement patterns, the accuracy in inferring participants' preference choices using EMSHMM is surprisingly and significantly higher than that using EMHMM. Advantageously, EMSHMM can better capture the cognitive processes involved in the task and consequently lead to higher inference accuracy.

Further advantageously, the instant methods can deduce participants' preference during a decision making process from eye gaze transition information alone. In contrast, previous methods needed to combine eye movement measures with other information such as additional physiological measures or attended visual features including integrated skin conductance, blood volume pulse, pupillary response.

Furthermore, while previous methods reached an average accuracy of 81%, the instant methods deduce participants' preference from eye gaze transition information alone using EMSHMM with more than 90% accuracies.

In addition, EMSHMM provides quantitative measures of similarities among individual eye movement patterns by calculating the log-likelihood of one's eye movement data being generated by a representative HMM. For example, it was shown that the similarity of participants' eye movement patterns during the preference-biased period to the representative pattern of group A as opposed to that of group B (as measured in A-B scale) was positively correlated with the gaze cascade effect and inference accuracy using fixations during the final 2 seconds before response. In addition to examining the relationship between eye movement patterns and other psychological measures, using methods of the instant invention it can also be determined how the eye movement pattern similarity measure is modulated by factors related to decision making styles, such as gender, cultural, sleep loss, etc. Using EMHMM, it was shown that eye movement pattern similarity to an eye-centered, analytic pattern during face recognition is associated with better recognition performance whereas similarity to a nose-centered, holistic patterns is correlated with cognitive decline in older adults (see e.g., Chuk, Chan, et al., 2017; Chuk, Crookes, et al., 2017; Chan et al., 2018), that individuals with insomnia symptoms exhibit eye movement patterns more similar to a representative nose-mouth pattern during facial expression judgments as compared with healthy controls (Zhang, Chan, Lau, & Hsiao, 2019). Advantageously, the EMSHMM of the instant invention can be used to examine how eye movement patterns are associated with other psychological measures and factors that may affect eye movement patterns in more complex tasks that involve cognitive state changes.

While the analysis using methods of the instant invention so far focused on the eye gaze transition behavior between two stimuli of choice in the preference decision-making task by using only two ROIs, with each corresponding to a stimulus, further methods are provided to analysis eye movement pattern, e.g., ROIs (low-level states) and transition probabilities among the ROIs, on each stimulus to capture individual differences in information extraction in addition to gaze transition in decision-making behavior. Previous studies showed that participants have preferred fixated features or fixation locations during subjective decision-making. For example, it was found that attractive and unattractive features received more attention than those with intermediate attractiveness and brands located at the center of a shelf in shops were more likely to be chosen. Because individuals differ in how they obtain information from the stimuli of choice during decision making, or in a cognitive task in general, the methods of the instant invention using an EMSHMM toolbox (see Chuk et al., 2014) capture these individual differences by inferring personalized ROIs on each stimulus using a Gaussian mixture model approach and enable the determination of the optimal number of ROIs for each participant trough the Bayesian method. Advantageously, using a larger number of high-level states, the EMSHMM method is able to discover more fine-grained cognitive states in between the exploration and preference-biased periods in terms of similarity. For example, in more complex cognitive tasks such as driving or cooking, with a large number of high-level states the instant method enables the detection of more discrete cognitive states essential to the task and their associated eye movement patterns.

The SHMM can represent differences in transition matrices within a trial (intra-trial differences), while other methods, e.g., the mixed HMM by Altman (2007), add random effects to the HMM. In particular, random effects are added to the emission density means and to the log-probabilities of the transition matrix and prior. This allows inter-subject or inter-trial differences to be represented in a single model. Thus, in some embodiments of the invention the SHMM are extended to add random effects to model inter-subject differences in a single model.

In summary, in some embodiments, the novel EMSHMM-based methods of the instant invention analyze eye movement data in tasks that involve cognitive state changes where for each participant an SHMM is used to capture between cognitive state transitions during the task, with eye movement patterns during each cognitive state being summarized using an HMM.

In some embodiments, the EMSHMM of the invention is applied to a face preference decision-making task. In specific embodiments, the EMSHMM of the invention identifies two common eye movement patterns from the participants, where one pattern entered the preference-biased cognitive state later, showed a stronger gaze cascade effect immediately before the decision response, and allowed the determination of the preference decision later in a trial and the other pattern revealed the preference decision much earlier in a trial, spent more time in the preference-biased cognitive state, had a weaker gaze cascade effect in the end, and led to a lower decision response inference accuracy.

These surprising differences emerged naturally as the result of clustering based on eye movement data alone, and were not revealed by any existing methods in the literature. As compared with previous approaches, the EMSHMM method of the invention is unexpectedly superior at capturing eye movement behavior in the task and infers participants' decision responses with higher accuracy. In addition, EMSHMM provides quantitative measures of similarities among individual eye movement patterns, and thus is particularly suitable for studies using eye movements to examine individual differences in cognitive processes, making a significant impact on the use of eye tracking to study cognitive behavior across disciplines.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Altman, R. (2007). Mixed hidden Markov models: An extension of the hidden Markov model to the longitudinal data setting. *Journal of the American Statistical Association*, 102, 201-210.

Andrews, T. J., & Coppola, D. M. (1999). Idiosyncratic characteristics of saccadic eye movements when viewing different visual environments. *Vision research*, 39(17), 2947-2953.

Castelhano, M. S., & Henderson, J. M. (2008). Stable individual differences across images in human saccadic eye movements. *Canadian Journal of Experimental Psychology*, 62(1), 1-14.

Chan, C. Y. H., Chan, A. B., Lee, T. M. C., & Hsiao, J. H. (2018). Eye movement patterns in face recognition are associated with cognitive decline in older adults. *Psychonomic Bulletin & Review*, 25(6), 2200-2207.

Chuk, T., Chan, A. B., & Hsiao, J. H. (2014). Understanding eye movements in face recognition using hidden Markov models. *Journal of Vision*, 14(11):8, 1-14.

Chuk, T., Chan, A. B., & Hsiao, J. H. (2017). Is having similar eye movement patterns during face learning and recognition beneficial for recognition performance? Evidence from hidden Markov modeling. *Vision Research*, 141, 204-216.

Chuk, T., Crookes, K., Hayward, W. G., Chan, A. B., & Hsiao, J. H. (2017). Hidden Markov model analysis reveals the advantage of analytic eye movement patterns in face recognition across cultures. *Cognition*, 169, 102-117.

Coviello, E., Chan, A. B., & Lanckriet, G. R. (2014). Clustering hidden Markov models with variational HEM. *The Journal of Machine Learning Research*, 15(1), 697-747.

Govaert, G., & Nadif, M. (2013). *Co-clustering: models, algorithms and applications*. ISTE, Wiley. ISBN 978-1-84821-473-6.

Kanan, C., Bseiso, D. N., Ray, N. A., Hsiao, J. H., & Cottrell, G. W. (2015). Humans have idiosyncratic and task-specific scanpaths for judging faces. *Vision research*, 108, 67-76.

Lau, E. Y. Y., Eskes G. A., Morrison, D. L., Rajda, M., Spun, K. F. (2010). Executive function in patients with obstructive sleep apnea treated with continuous positive airway pressure. *J. Int. Neuropsych. Soc.*, 16, 1077-1088.

MacQueen, J. (1967). Some methods for classification and analysis of multivariate observations. In Proceedings of the Fifth Berkeley Symposium on Mathematical Statistics and Probability (pp. 281-297'. Berkeley, Calif.: University of California Press.

Phillips, L. H., Wynn, McPherson, S., & Gilhooly, K. J. (2001). Mental planning and the Tower of London task. *Q. J. Exp. Psychol.—A*, 54, 579-597

Poynter, W., Barber, M., Inman, J., & Wiggins, C. (2013). Individuals exhibit idiosyncratic eye-movement behavior profiles across tasks. *Vision research*, 89, 32-38.

Ridderinkhof, K. R., Band, G. P., & Logan, D. (1999). A study of adaptive behavior: effects of age and irrelevant information on the ability to inhibit one's actions. *Acta Psychol.*, 101, 315-337.

Shimojo, S., Simion, C., Shimojo, E., & Scheier, C. (2003). Gaze bias both reflects and influences preference. *Nature neuroscience*, 6(12), 1317-1322.

Wu, D. W. L., Bischof, W. F., Anderson, N. C., Jakobsen, T., & Kingstone, A. (2014). The influence of personality on social attention. *Personality and Individual Differences*, 60, 25-29.

Yeung, P. Y., Wong, L. L., Chan, C. C., Leung, J. L., & Yung, C. Y. (2014). A validation study of the Hong Kong version of Montreal Cognitive Assessment (HK-MoCA) in Chinese older adults in Hong Kong. *Hong Kong Med. J.*, 20(6), 504-510.

Zhang, J., Chan, A. B., Lau, E. Y. Y., & Hsiao, J. H. (2019). Individuals with insomnia misrecognize angry faces as fearful faces while missing the eyes: An eye-tracking study. *Sleep*, 42(2), zsy220.

We claim:

1. An eye movement analysis with hidden Markov model (EMHMM) with co-clustering comprising:
    a vector of prior values of hidden states, a transition matrix of the hidden states, and
    a Gaussian emission for each hidden state; wherein the prior values indicate the probabilities of time-series data starting from a corresponding hidden state; the transition matrix indicates the transition probabilities between any two hidden states; and the Gaussian emissions indicate the probabilistic associations between an observed time-series data and a hidden state; and
    a co-clustering data mining technique;
    wherein the EMHMM with co-clustering analyzes eye movement data involving stimuli with different feature layouts, and
    wherein the co-clustering data mining technique is configured to cluster the eye movement data into groups and assess each individual's data log-likelihoods based on co-clustering eye movement group models.

2. An eye movement analysis with switching hidden Markov model (EMSHMM) comprising:
    a vector of prior values of hidden states, a transition matrix of the hidden states, and
    a Gaussian emission for each hidden state; wherein the prior values indicate the probabilities of time-series data starting from a corresponding hidden state; the transition matrix indicates the transition probabilities between any two hidden states; and the Gaussian emissions indicate the probabilistic associations between an observed time-series data and a hidden state; and
    two levels of hidden state sequences comprising: several low-level hidden state sequence models that are used to learn the eye movement pattern of several cognitive states and a high-level hidden state sequence model that acts like a switch that captures the transitions between cognitive states;
    wherein the EMSHMM analyzes eye movement data in complex tasks that involve cognitive state changes,
    wherein the EMSHMM is based on aggregated SHMM from the two separately trained SHMMs.

3. A method for determining a cognitive style and/or cognitive ability in a subject, the method comprising:
  collecting eye movement data of a subject;
  computing regions of interest (ROIs) based on the eye movement data;
  measuring transition times between the ROIs;
  calculating transition probabilities among the ROIs;
  clustering eye movements into groups using co-clustering;
  assessing each individual's data log-likelihoods using the co-clustering eye movement group models;
  measuring executive function using TOL, visual attention using Flanker Task, working memory using Verbal and Visuospatial Two-Back Task;
  determining the relationship between data log-likelihood measures and measured executive function, visual attention, and working memory; and
  determining a cognitive style and/or cognitive ability of the subject based on the data log-likelihood measures using the co-clustering eye movement group models, or the eye movement group to which the subject's eye movement was co-clustered.

4. A method for determining the cognitive state in a subject, the method comprising:
  collecting eye movement data of a subject;
  computing regions of interest (ROIs) based on the eye movement data;
  measuring transition times between the ROIs;
  calculating transition probabilities using the EMSHMM according to claim 2; and
  determining the cognitive state of the subject based on the EMSHMM results.

5. A method for inferring a subject's choice, the method comprising:
  providing two image choices;
  collecting eye movement data of a subject looking at the two image choices;
  computing regions of interest (ROIs) based on the eye movement data;
  measuring transition times between the ROIs;
  calculating transition probabilities among the ROIs;
  training one switching hidden Markov model (SHMM) for a first chosen image and one SHMM for a second chosen image;
  generating an aggregated SHMM from the two trained SHMMs;
  calculating the probability of a last fixation based on the aggregated SHMM; and
  inferring a choice based on the calculated probability and the subject's last fixation.

6. An electronic device for determining a cognitive style in a subject, the device comprising:
  a camera configured to capture a facial image; and
  a processor configured to detect a center position of an eye within a facial image via the camera, to determine an eye gaze position based on the center position and a pupil position, to analyze the eye gaze position in consecutively captured facial images, and to measure an eye movement patterns based on the eye gaze positions of the consecutively captured facial images;
  wherein the processor is further configured to calculate a log likelihood of an eye movement pattern and to assign a certain cognitive style to the measured eye movement pattern if it matches the eye movement pattern of a representative group of subjects having the certain cognitive style, and
  wherein the processor is configured to cluster the eye movement data into groups and assess each individual's data log-likelihoods based on co-clustering eye movement group models.

7. The device according to claim 6, wherein the processor is further configured to receive external user-entered data that assign certain eye movement patterns with certain external task criteria and/or cognitive state criteria; and the processor is configured to assign a cognitive state to the subject based on the external task criteria and/or cognitive state criteria and the subject's eye movement patterns.

* * * * *